(12) United States Patent
DeStefano

(10) Patent No.: US 9,352,115 B1
(45) Date of Patent: May 31, 2016

(54) RESPIRATORY VENTILATION SYSTEM WITH GAS SPARING VALVE HAVING OPTIONAL CPAP MODE AND MASK FOR USE WITH SAME

(71) Applicant: NeoForce Innovations, LLC, Ivyland, PA (US)

(72) Inventor: Mark DeStefano, Collegeville, PA (US)

(73) Assignee: Capnia, Inc., Redwood City, CA (US)

( * ) Notice: Subject to any disclaimer, the term of this patent is extended or adjusted under 35 U.S.C. 154(b) by 536 days.

(21) Appl. No.: 13/680,793

(22) Filed: Nov. 19, 2012

Related U.S. Application Data

(60) Provisional application No. 61/561,465, filed on Nov. 18, 2011.

(51) Int. Cl.
*A61M 16/06* (2006.01)
*A61M 16/20* (2006.01)

(52) U.S. Cl.
CPC ............. *A61M 16/20* (2013.01); *A61M 16/06* (2013.01); *A61M 16/0677* (2014.02)

(58) Field of Classification Search
CPC .............. A61M 16/20; A61M 16/207; A61M 16/0677; A61M 16/00; A61M 16/205; A61M 16/204; A61M 16/101; A61M 16/0666; A61M 16/0672; A62B 7/04; F16K 31/26; F16K 31/0627

USPC ............ 128/200.24, 201.28, 203.11, 204.18, 128/204.21, 204.23, 204.26, 205.11, 128/205.24, 205.25, 206.21, 207.12, 207.16
See application file for complete search history.

(56) References Cited

U.S. PATENT DOCUMENTS

| | | | | |
|---|---|---|---|---|
| 4,054,133 | A | * 10/1977 | Myers | 128/204.26 |
| 4,838,257 | A | * 6/1989 | Hatch | 128/204.18 |
| 5,368,021 | A | * 11/1994 | Beard et al. | 128/205.12 |
| 5,890,490 | A | * 4/1999 | Aylsworth et al. | 128/203.12 |
| 2006/0219245 | A1 | * 10/2006 | Holder | A61M 16/0666 128/204.26 |

* cited by examiner

*Primary Examiner* — Annette Dixon
(74) *Attorney, Agent, or Firm* — Blank Rome LLP

(57) ABSTRACT

A system for delivering gas to a patient. The system includes a gas control unit, a breathing circuit, a control switch, and a patient interface. The gas control unit has a main gas outlet. The breathing circuit has a main gas line having a first end. The first end of the main gas line is coupled to the main gas outlet. The control switch may be a pneumatic switch, in which case the breathing circuit further has a pilot control line for pneumatically controlling the gas control unit to deliver gas to the main gas line via the main gas outlet. The control switch may be an electrical switch, in which case the breathing circuit may use electrical control of the gas delivery or electrical and pneumatic control of the gas delivery. Other embodiments of the gas control unit may include a continuous positive airway pressure branch.

18 Claims, 23 Drawing Sheets

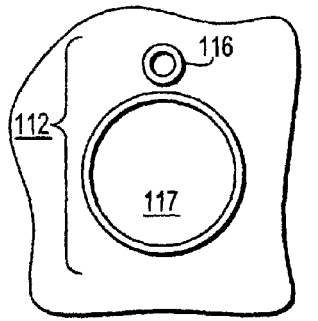
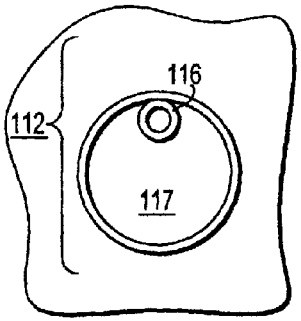
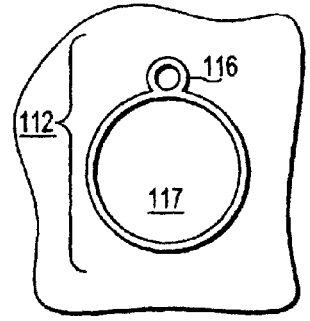
FIG. 5A    FIG. 5B    FIG. 5C
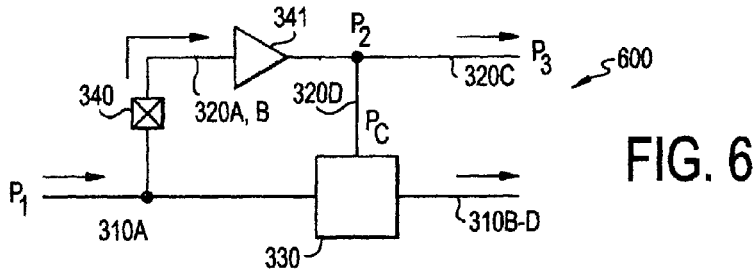
FIG. 6
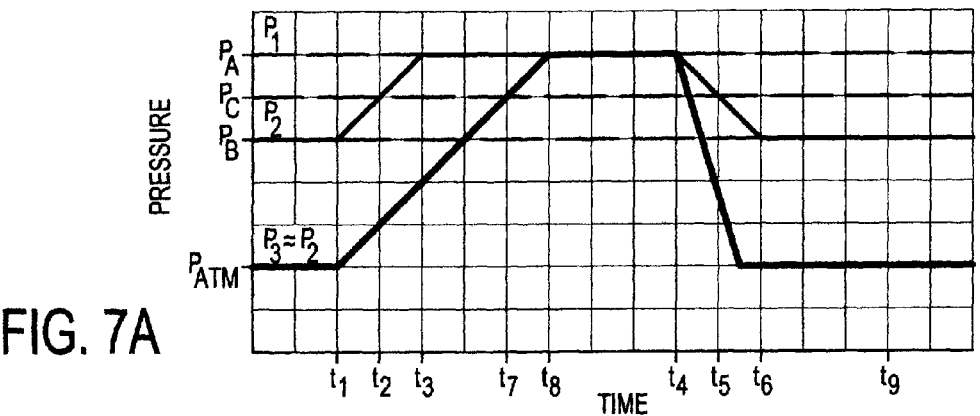
FIG. 7A
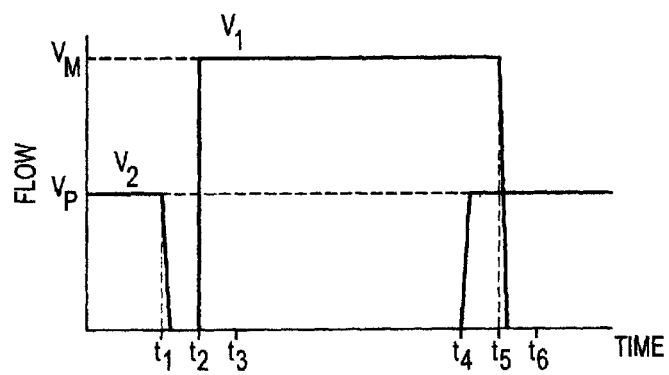
FIG. 7B

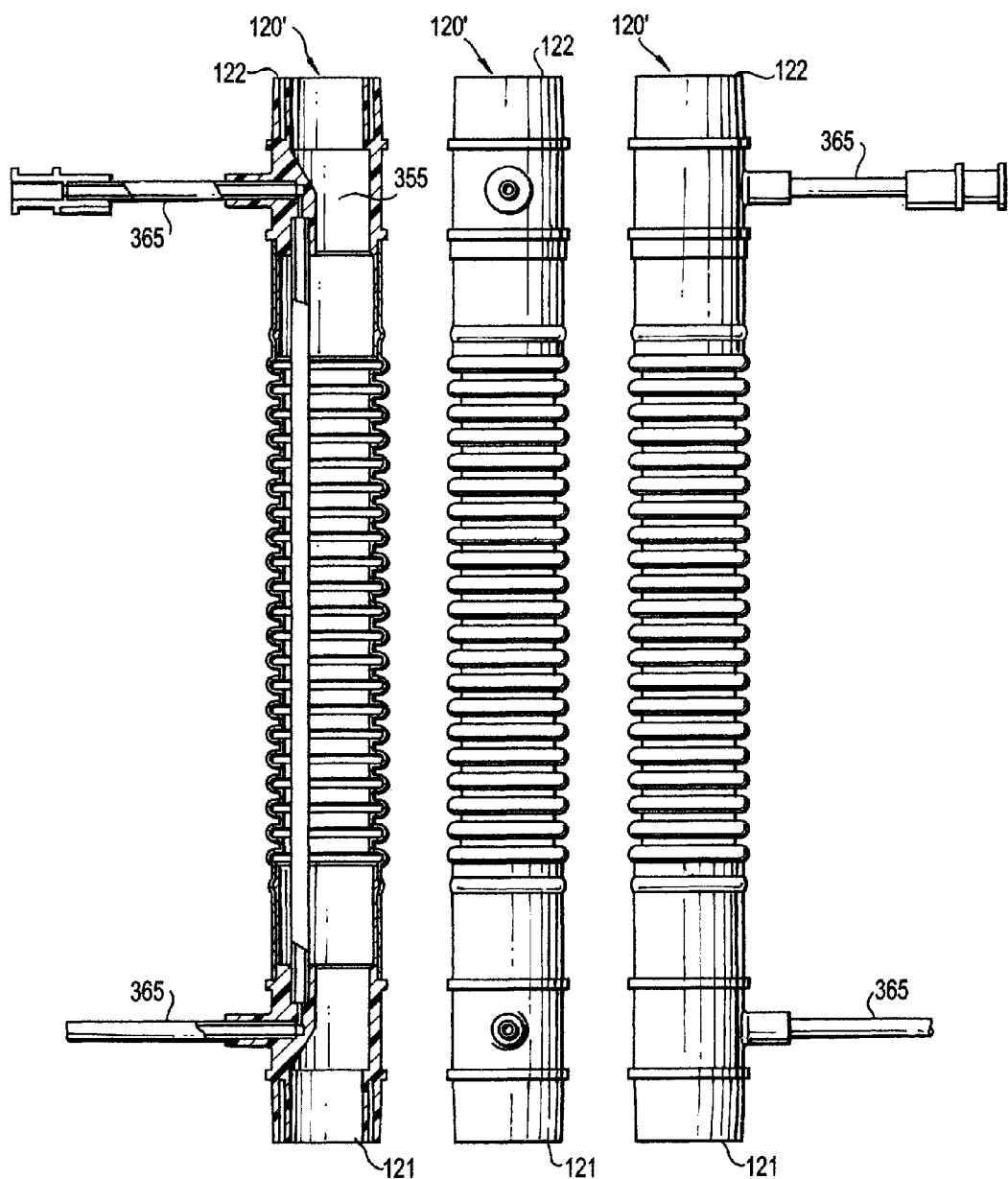

BEFORE PRESSURE DAMPER

AFTER PRESSURE DAMPER

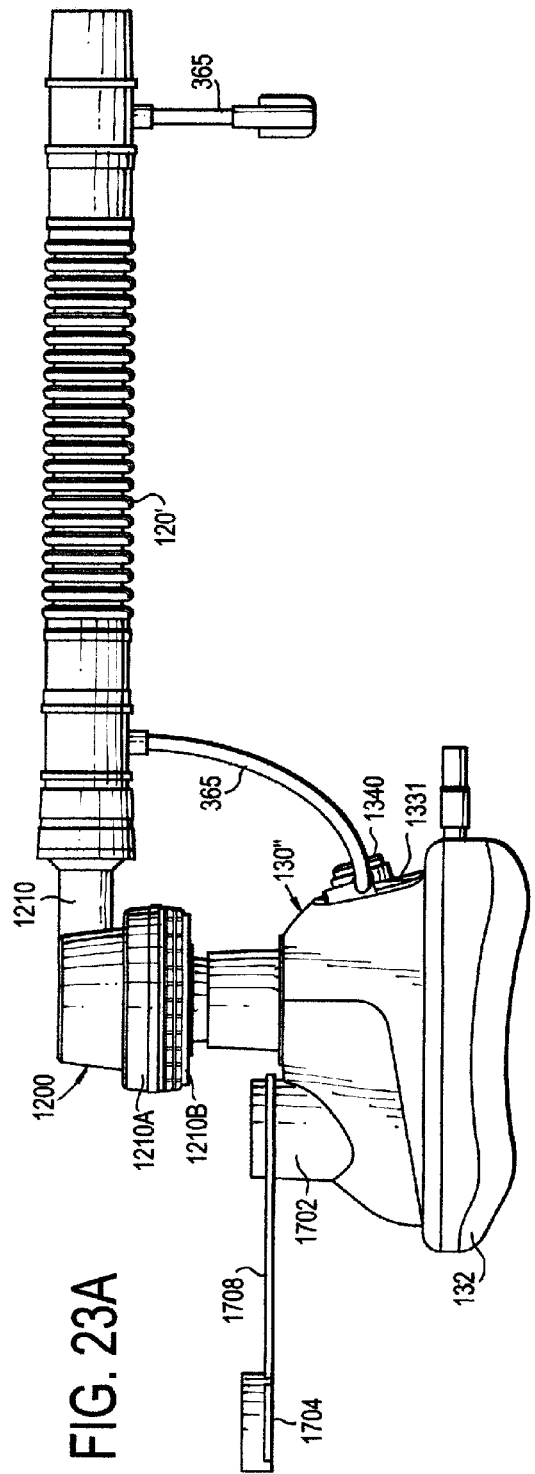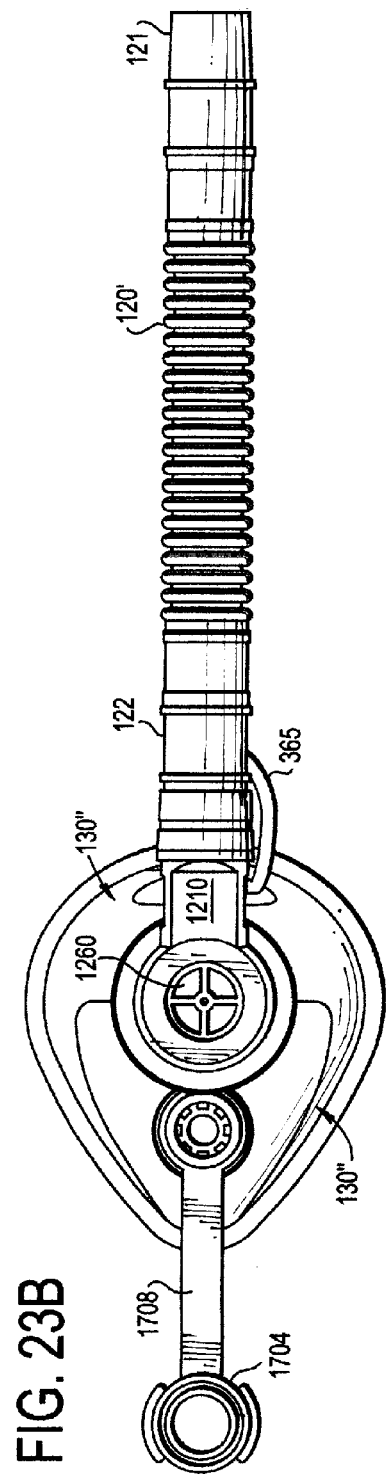

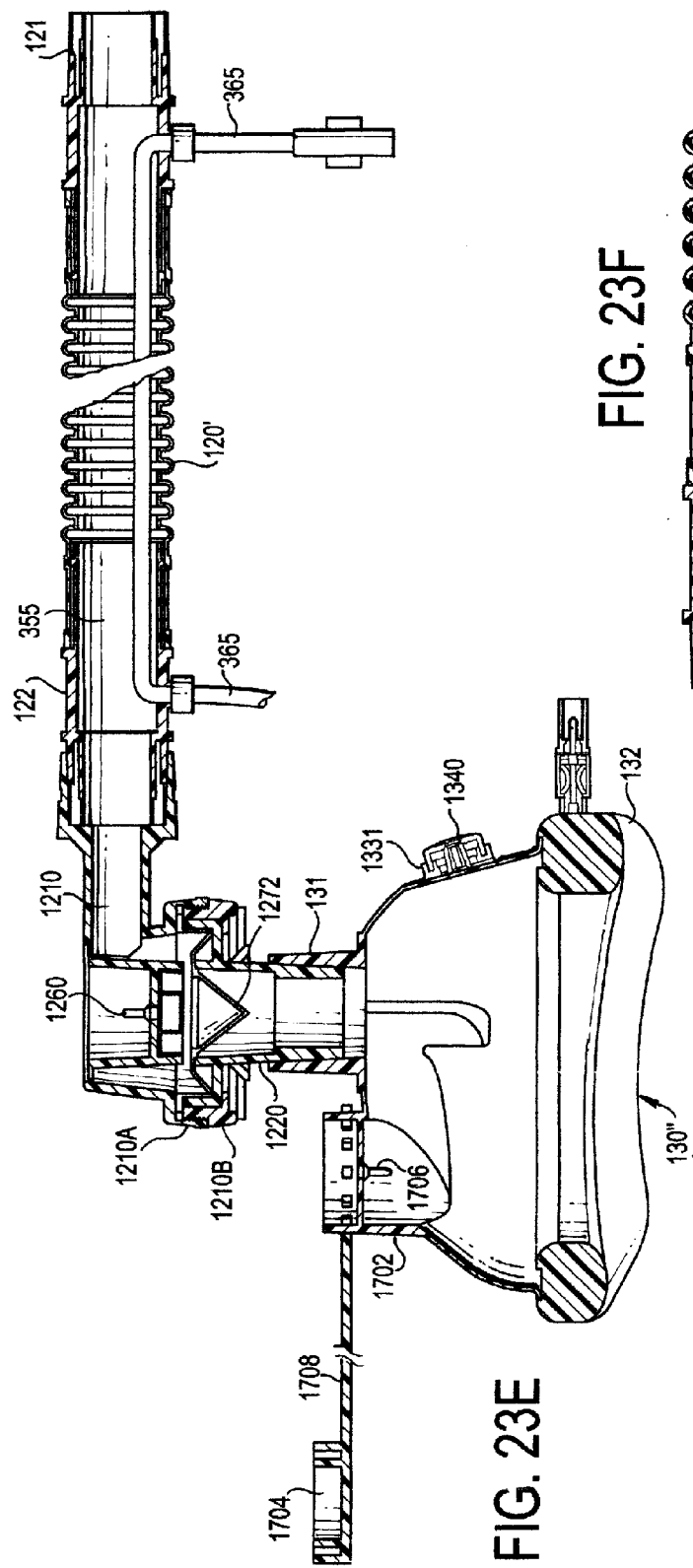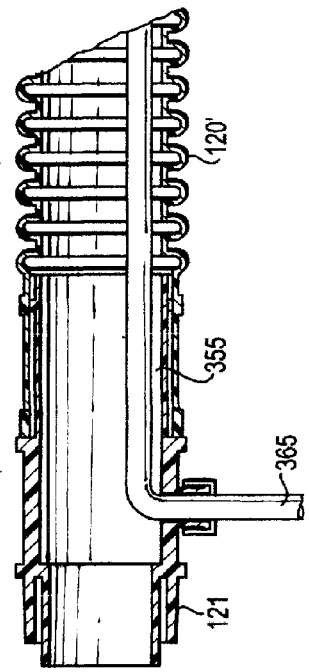
FIG. 23E
FIG. 23F

RESPIRATORY VENTILATION SYSTEM WITH GAS SPARING VALVE HAVING OPTIONAL CPAP MODE AND MASK FOR USE WITH SAME

CROSS REFERENCE TO RELATED APPLICATION

This application claims the benefit of U.S. Provisional Application No. 61/561,465, entitled "Respiratory Ventilation System with Gas Sparing Valve Having Optional CPAP Mode" and filed Nov. 18, 2011, the contents of which application are incorporated herein by reference.

FIELD OF THE INVENTION

The present invention relates, generally, to a respiratory ventilation system that controls gas delivery to a patient and, particularly, to a respiratory ventilation system that utilizes a gas sparing valve to conserve gas. More particularly, the present invention relates to a pneumatically controlled respiratory ventilation system that utilizes a pilot circuit to control gas flow in a main gas supply circuit to thereby conserve gas supplied to a patient.

BACKGROUND OF THE INVENTION

Ventilation is the physiologic process of moving a gas into (inspiration) and out of (expiration) the lungs of a patient, thereby delivering oxygen to organs of the patient and excreting carbon dioxide. During spontaneous ventilation, i.e. unassisted breathing, negative (sub-atmospheric) pressure is created within the chest of the patient. As a result, gas moves into the lungs of the patient.

In the practice of medicine, there is often a need to substitute mechanical ventilatory support for the spontaneous breathing of a patient. Mechanical ventilation is a method to mechanically assist or replace spontaneous breathing. This may involve a machine called a ventilator. Alternatively, the breathing of the patient may be assisted by a physician or other suitable person compressing a bag or set of bellows. In positive pressure ventilation, air (or another gas mix, e.g., oxygen mix) is pushed into the trachea of the patient. The positive pressure forces air to flow into the airway to expand and fill the lungs until the inspiration breath is terminated. Subsequently, the airway pressure drops, and the elastic recoil of the chest wall and lungs push the tidal volume, the breath, out through passive expiration or exhalation.

Mechanical ventilation may be necessary during respiratory failure or when patients are placed under anesthesia. Particular examples are patients with acute lung injury, including acute respiratory distress syndrome (ARDS); apnea with respiratory arrest, including cases from intoxication; chronic obstructive pulmonary disease (COPD); acute respiratory acidosis; respiratory distress; hypoxemia; hypotension including sepsis; shock; congestive heart failure; and neurological diseases such as Muscular Dystrophy and Amyotrophic Lateral Sclerosis; etc.

SUMMARY OF THE INVENTION

In accordance with an exemplary aspect of the present invention, there is provided a system for delivering gas to a patient. The system includes a gas control unit, a breathing circuit, a pilot control switch, and a patient interface. The gas control unit includes an outlet having a main gas line outlet. The gas control unit further includes a gas sparing circuit having a primary branch coupled to the main gas line outlet. The primary branch includes a gas sparing valve for controlling a flow of gas through the primary branch. The breathing circuit includes a main gas line having a first end and a second end. The first end of the main gas line is coupled to the main gas line outlet. The pilot control switch is for selectively causing the gas sparing valve to provide the flow of gas to the main gas line via the main gas line outlet. The patient interface is coupled to the second end of the main gas line of the breathing circuit.

In accordance with another exemplary aspect of the present invention, there is provided a pneumatic system for delivering gas to a patient. The pneumatic system includes a gas control unit, a breathing circuit, a pilot control switch, and a patient interface. The gas control unit includes an outlet having a pilot control line outlet and a main gas line outlet. The breathing circuit includes a pilot control line having a first end and a second end. The breathing circuit also includes a main gas line having a first end and a second end. The first end of the pilot control line is coupled to the pilot control line outlet, and the first end of the main gas line is coupled to the main gas line outlet. The pilot control switch allows a user to selectively cause the gas control unit to provide gas to the main gas line via the main gas line outlet. The patient interface is coupled to the second end of the main gas line of the breathing circuit.

In accordance with a further exemplary aspect of the present invention, there is provided a pneumatic system for delivering gas to a patient. The pneumatic system includes a gas control unit, which includes an outlet having a pilot control line outlet and a main gas line outlet and a gas sparing circuit. The gas sparing circuit includes a primary branch coupled to the main gas line outlet, a pilot control branch coupled to the pilot control line outlet, a pneumatic control valve disposed in the primary branch, the pneumatic control valve comprising a control input, and a timer circuit comprising an output coupled to the control input of the pneumatic control valve. The pneumatic system also includes a breathing circuit having a pilot control line a main gas line. The pilot control line includes a first end and a second end, and the main gas line includes a first end and a second end. The first end of the pilot control line is coupled to the pilot control line outlet, and the first end of the main gas line is coupled to the main gas line outlet. The pneumatic system further includes a pilot control switch for selectively causing the pneumatic control valve to open to provide gas to the main gas line via the main gas line outlet and for activating the pneumatic timer to close the pneumatic control valve after a predetermine amount of time. A patient interface is coupled to the second end of the main gas line of the breathing circuit.

In accordance with still another exemplary aspect of the present invention, there is provided a pneumatic system for delivering gas to a patient. The pneumatic system includes a gas control unit having an outlet including a pilot control line outlet and a main gas line outlet. The pneumatic system also includes a breathing circuit, a pilot control switch, and an endotracheal hand piece configured to couple the breathing circuit to an endotracheal tube. The breathing circuit includes a pilot control line having a first end and a second end and a main gas line having a first end and a second end. The first end of the pilot control line is coupled to the pilot control line outlet, and the first end of the main gas line is coupled to the main gas line outlet. The pilot control switch allows for a user to selectively cause the gas control unit to provide gas to the main gas line via the main gas line outlet.

In accordance with yet another exemplary aspect of the present invention, there is provided a pneumatic system for delivering gas to a patient. The pneumatic system includes a gas control unit, a breathing circuit, a pilot control switch, and a patient interface. The gas control unit includes a pilot branch, a primary branch, a continuous positive airway pressure (CPAP) branch, and an outlet having a pilot control line outlet coupled to the pilot branch and a main gas line outlet coupled to the primary branch and the CPAP branch. The gas control unit further includes a directional flow control valve for selecting for gas to flow to the main gas line outlet via the primary branch or the CPAP branch. The breathing circuit includes a pilot control line having a first end and a second end and a main gas line having a first end and a second end. The first end of the pilot control line is coupled to the pilot control line outlet, and the first end of the main gas line is coupled to the main gas line outlet. The pilot control switch allows a user to selectively cause the gas control unit to provide gas to the main gas line via the main gas line outlet. The patient interface is coupled to the second end of the main gas line of the breathing circuit.

In accordance with another aspect of the present invention, there is provided a gas control unit. In one embodiment, the gas control unit includes an outlet having a main gas line outlet, and a gas sparing circuit including a primary branch coupled to the main gas line outlet and a gas sparing valve for controlling a flow of gas through the primary branch in response to a selective control. In another embodiment, the gas control unit includes an inlet line, an outlet port having a pilot control line outlet and a main gas line outlet, and a gas sparing circuit. The gas sparing circuit includes a primary branch coupled to the inlet line and the main gas line outlet, a pilot control branch coupled to the inlet line and the pilot control line outlet, and a pneumatic control valve disposed in the primary branch. The pneumatic control valve includes an input coupled to the inlet line, an output coupled to the main gas line outlet, and a control input coupled to the pilot branch. The pneumatic control valve is configured to be actuated after occlusion of the pilot control branch to allow gas to flow through the primary branch to the main gas line outlet.

In accordance with yet another embodiment of the present invention, there is provided a valve system having a one-way breathing valve for providing primary gas from a source system to a patient upon inhalation, a one-way exhaust valve for exhausting gas from the patient upon exhalation, and an air inlet valve for inletting gas from atmosphere when demand for gas from the patient during inhalation exceeds the gas from the source system.

In accordance with yet another embodiment of the present invention, there is provided a patient interface for use with a gas sparing circuit. The patient interface may include a patient mask interface or an endotracheal tube connection. The patient interface may also include a vent port for exhalation by a user of the patient interface during a continuous positive airway pressure (CPAP) mode.

BRIEF DESCRIPTION OF THE DRAWINGS

For the purpose of illustration, there are shown in the drawings certain embodiments of the present invention. In the drawings, like numerals indicate like elements throughout. It should be understood, however, that the invention is not limited to the precise arrangements, dimensions, and instruments shown. In the drawings:

FIGS. 5A through 5C illustrate various exemplary embodiments of an external gas port used with the gas control units of FIGS. 1 and 2, the external gas port comprising pilot and main outlets, in accordance with an exemplary embodiment of the present invention;

FIG. 6 illustrates an exemplary simplified block diagram of the exemplary embodiment of the gas sparing circuit of FIG. 1 or FIG. 2, in accordance with an exemplary embodiment of the present invention;

FIG. 7A illustrates a graph of exemplary pressures at various points in the exemplary simplified block diagram illustrated in FIG. 6, in accordance with an exemplary embodiment of the present invention;

FIG. 7B illustrates a graph of exemplary gas flow through the primary branch and the pilot control branch in the gas sparing circuit of FIG. 1 or FIG. 2, in accordance with an exemplary embodiment of the present invention;

FIGS. 8C through 8E illustrate various views of an exemplary alternative embodiment of a disposable breathing circuit, in accordance with an exemplary embodiment of the present invention;

FIGS. 23A through 23F illustrate various views of various components of a combination of the mask of FIGS. 22A through 22C connected to the mask connection of FIG. 12, which is connected to the exemplary alternative embodiment of the disposable breathing circuit of FIG. 8C, in accordance with an exemplary embodiment of the present invention;

DETAILED DESCRIPTION OF THE INVENTION

Conventional pneumatic flow circuits or devices do not allow for resuscitation gas flow to be controlled pneumatically. Although it is possible to put a spring-actuated flow control valve near an outlet point of a conventional pneumatic flow circuit, this placement of the flow control valve would make the pneumatic flow circuit complicated and bulky. Further, because the portion of the pneumatic flow circuit connected to the patient may be disposable, placement of the flow control valve on the disposable portion would result in a possibly unacceptable increase in cost of the disposable portion. Further, locating the flow control valve in the disposable portion may not allow for a pop off and peak inspiratory pressure (PIP) pressure control valve arrangement with a gauge remotely located within the pneumatic flow circuit. If located after the flow control valve in the disposable portion, such components would make the disposable portion bulky and expensive. Locating such pressure control valve arrangement at the patient site may increase the size and cost of the disposable portion.

Conventional manual and pneumatic devices suffer from numerous disadvantages, such as continuous large gas flows, no flow control, and no pressure control. In addition, some devices waste significant amounts of compressed gases, thereby causing compressed gas tanks to have very limited life. Furthermore, conventional pneumatic devices do not offer the option of delivering fixed, user set flow rates in a continuous positive airway pressure (CPAP) mode through a combined resuscitation and CPAP unitary breathing circuit and mask assembly.

An exemplary embodiment of the present invention provides a gas sparing circuit that minimizes the continuous large gas flows from conventional pneumatic devices while allowing for user activation of the large gas flows required for resuscitation. In addition, the gas sparing circuit allows for precise pressure and volume control to the patient currently not available in conventional resuscitation devices.

Figure 1:
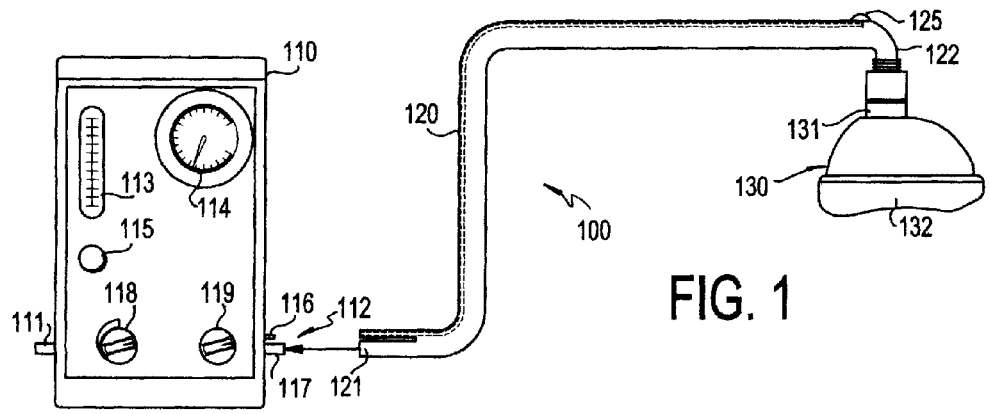
FIG. 1 illustrates an exemplary embodiment of a system for delivering gas to a patient, the system comprising a gas control unit, a disposable breathing circuit, and a mask, the gas control unit comprising a gas sparing circuit comprising a primary branch and a pilot control branch, the primary branch comprising a gas sparing valve, in accordance with an exemplary embodiment of the present invention.

Referring now to FIG. 1, there is illustrated a block diagram of a system, generally designated as 100, for delivering gas to a patient, in accordance with an exemplary embodiment of the present invention. The system comprises a gas control unit 110, a disposable breathing circuit 120, and a patient mask 130. The disposable breathing circuit 120 operates in a resuscitation mode to deliver resuscitating gas to a patient (not illustrated) via a patient mask 130 worn by the patient. A first end 121 of the disposable breathing circuit 120 is coupled to the gas control unit 110, and a second end 122 of the disposable breathing circuit 120 is coupled to a connection port 131 of the patient mask 130 to deliver gas to the patient during inhalation. The mask 130 interfaces with the patient via a patient-mask interface 132. A pilot control switch 125 is disposed near the end 122 of the disposable breathing circuit 120 for selective control of main gas delivery flow to the patient. In one exemplary embodiment, the gas comprises air. In another exemplary embodiment, the gas comprises an oxygen mixture. Although not illustrated, it is to be understood that, in an exemplary embodiment, the mask 130 may include one or more exhaust ports to allow for exhalation by the patient.

The basic principle of operation for the system 100 is to utilize a pneumatic pilot controlled valve in the gas control unit 110. As discussed below with respect to FIG. 3, the pneumatic pilot controlled valve is coupled to a high pressure, low flow small diameter pilot control circuit that is controlled by a user, such as a medical practitioner, to control a high pressure, high flow main gas circuit to provide on-demand high flow to the patient when needed and to only allow a small trickle pilot flow when there is no main gas demand. This control conserves gas supply by closing the main gas circuit when not demanded. Demanded gas flows at a rate of 35 to 50 liters/minute. A trickle flow of 1-3 liters/minute flows through the pilot control circuit when there is no main gas demand or need for gas by the patient. In an exemplary embodiment, pilot gas flows through the pilot control circuit at not more than 2 liters per minute.

Accordingly, the gas control unit 110 comprises a gas inlet 111 and a gas port 112 comprising a pilot control port 116 and a main gas port 117. (As used herein, the terms "port," "outlet," and "outlet port" may be used interchangeably herein as context permits. The same holds true for the terms "port," "inlet," and "inlet port" and the terms "primary gas," "main gas," and "patient gas.") The gas inlet 111 is coupled to a gas source (supply), such as a wall source, compressed gas line, or a canister of compressed breathing gas. The pilot control port 116 is coupled to a pilot control line, and the main gas outlet 117 is coupled to a high pressure, high flow main gas line. The gas control unit 110 includes a flow rate control selection means 115 to allow the user to select a desired flow rate in the main gas line. An example of selection means 115 is a flow control valve. The gas control unit 110 further comprises a flow meter 113 to display the current flow rate of the gas through the inlet 111 and a pressure gauge 114 to display the current gas pressure in the main gas outlet 117 being delivered to the patient. The gas control unit 110 also comprises a pop off maximum pressure relief valve 118 and a peak inspiratory pressure (PIP) relief valve 119. Although the gas control unit 110 is configured for receiving gas from an external gas source via the inlet 111, other exemplary embodiments are contemplated. For example, it is contemplated that the gas control unit 110 may comprise an internal gas source, such as an internal tank, for storing primary gas, or internal gas pump.

The maximum pressure relief valve 118 allows the user to set the maximum pressure that can build up in the gas control unit 110 and the disposable breathing circuit 120 before safely venting to atmosphere. It ensures that pressure in the system 100 does not exceed this maximum pressure. Thus, the valve 118 protects the patient from the high main gas source outlet pressure, typically 50 psi.

The peak inspiratory pressure (PIP) valve 119 allows the user to set the peak inspiratory pressure the patient will be exposed to. Thus, the PIP valve 119 protects the patient from gas delivery pressures above PIP pressure. In the event that gas pressure at the main gas outlet 117 is above PIP, the PIP valve 119 opens to maintain the pressure at the outlet 117 at the PIP setting to ensure that the pressure of the gas delivered to the mask 130 is safe for the patient's lungs. The valve 118 acts as a safety valve in the event that the PIP valve 119 fails to properly operate.

Figure 3:
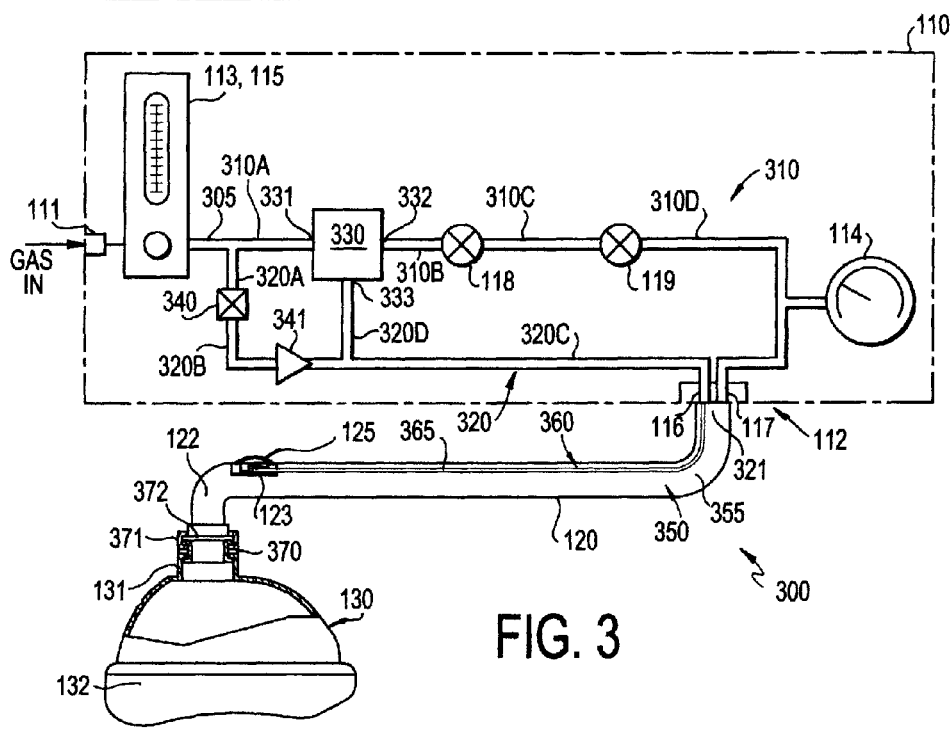
FIG. 3 illustrates an exemplary block diagram of the exemplary embodiment of the system of FIG. 1, in accordance with an exemplary embodiment of the present invention.

Referring now to FIG. 3, there is illustrated a block diagram of a gas sparing circuit 300 comprising the gas control unit 110, the disposable breathing circuit 120, and the patient mask 130, in accordance with an exemplary embodiment of the present invention. The gas sparing circuit 300 uses all of the components illustrated in FIG. 1 and additional components, as illustrated in FIG. 3.

The gas control unit 110 comprises a primary branch 310 comprising portions or lines 310A-310E and a secondary branch 320. The secondary branch is a pilot control branch 320 comprising portions or lines 320A-320D. The primary branch 310, specifically the portion 310A of the primary branch 310, is coupled to the gas inlet 111 via an inlet portion or line 305. The flow meter 113 and the flow rate control 115, which may be separate components or a unitary device, as illustrated in FIG. 3, are disposed within the inlet portion 305. The flow meter 113 displays the flow rate of supply gas through the gas inlet 111, and the flow rate control 115 allows a user or operator to modify this flow rate. In an exemplary embodiment, the portions 305, 310A-E, and 320A-D are respective tubes. As used herein, a user or operator may be the patient receiving gas or may be a person, such as a medical practitioner, who operates a gas control unit for benefit of a patient.

The portion 310A couples the primary branch 310 to the inlet portion 305 and is coupled to a primary flow inlet 331 of a pilot activated gas sparing valve 330 (also referred to herein as "pilot valve 330" or "pneumatic control valve 330"). The gas sparing valve 330 additionally comprises a primary flow outlet 332 and a pilot control input 333. The gas sparing valve 330 is normally closed, i.e., when the pressure at the pilot control input 333 is below a threshold pressure required to active the gas sparing valve 330, the gas sparing valve 330 is closed, and no primary gas flows from the primary flow inlet 331 to the primary flow outlet 332.

As described in more detail below, the pilot activated gas sparing valve 330 is controlled by the pilot control branch 320 to cause primary gas to flow through the primary flow outlet 332 of the valve 330. Such outputted gas flows through a portion 310B of the primary branch 310, through the pop off pressure relief valve 118, through a portion 310C of the primary branch 310, through the PIP pressure relief valve 119, and through portions 310D-310E of the primary branch 310 to the main gas outlet 117.

The pilot control branch 320, specifically the portion 320A of the pilot control branch 320, is coupled to the gas inlet 111 via the inlet portion 305. The portion 320A connects through a check valve 340 to a portion 320B. The portion 320B is connected to a portion 320C via an element 341 for pilot flow reduction. In an exemplary embodiment, the valve 341 is an orifice flow control element. In another exemplary embodiment, the valve 341 is a needle valve. The portion 320C is connected to the pilot control port 116.

The pilot control branch 320 is coupled to the control input 333 via a portion 320D of the pilot control branch 320, which portion 320D is tapped into the portion 320C. As is discussed in further detail below, the pilot control branch 320 controls the gas sparing valve 330 via the pilot control input 333.

Additional details regarding the disposable breathing circuit 120 are illustrated in FIG. 3 and are now described. The disposable breathing circuit 120 comprises a main gas line 355 (also referred to herein as a "primary gas line 355") comprising a first end 121 and a second end 122. The first end 121 of the main gas line 355 is coupled to the main gas outlet 117 for delivering source gas to the patient. The disposable breathing circuit 120 further comprises a pilot control line 365 comprising a first end 121 and a second end 123. The first end 121 of the pilot control line 365 is coupled to the pilot control port 116. The pilot control line 365 traverses the disposable breathing circuit 120 from the first end 121 to the pilot air flow control switch 125 at the second end 123. Located at the end 123 of the pilot control line 365 at the switch 125 is a vent port 351, which vents the end 123 of the pilot control line 365 to atmosphere. It is to be understood that the end 123 of the pilot control line 365 and, therefore, the pilot air flow control switch 125 may be disposed at any place along the disposable breathing circuit 120. In an exemplary embodiment, the end 123 of the pilot control line 365 and, therefore, the pilot air flow control switch 125 are disposed near the end 122 of the disposable breathing circuit 120 for convenience of use by the user activating the device for the patient wearing the mask 130.

As also illustrated in FIG. 3, the second end 122 of the disposable breathing circuit 120 is coupled to the mask 130 via a mask connection 370. In an exemplary embodiment, the mask connection 370 comprises a non-rebreathing element 371 which comprises a flow in/vent out configuration 372, which may include one or more exhaust ports to allow for exhalation by the patient. In an exemplary alternative embodiment, the one or more exhaust ports may be included in the mask 130 itself.

The pilot activated gas sparing valve 330 is controlled by the pressure in the portion 320D at the pilot control input 333 of the gas sparing valve 330. When the pressure at the pilot control input 333 reaches a threshold pressure, the valve 330 actuates and opens, thereby allowing full primary gas flow. When the pressure at the pilot control input 333 decreases below the threshold activating pressure, the valve 330 deactivates and closes, thereby stopping full primary gas flow.

The primary branch 310 and the main gas line 355 together form a main gas circuit 350 for delivering gas to a patient. The pilot control branch 320 and the pilot control line 365 together form a pilot control circuit 360 for controlling the delivery of gas in the main gas circuit 350. By using a main gas circuit 350 and a pilot control circuit 360 coupled to the same inlet 111, the same inlet gas flow is used to charge the main gas circuit 350 and the pilot control circuit 360. It is to be understood that description herein of occluding, un-occluding, charging, and venting the pilot control circuit 360 may be referred to as occluding, un-occluding, charging, and venting portions of the pilot control circuit 360, such as the pilot control branch 320 or the pilot control line, and vice versa.

FIGS. 5A through 5C illustrate alternative exemplary embodiments of the gas port 112, in accordance with an exemplary embodiment of the present invention. In a first exemplary embodiment illustrated in FIG. 5A, the pilot control port 116 is separate from the main gas port 117. In a second exemplary embodiment illustrated in FIG. 5B, the pilot control port 116 is disposed within the main gas port 117 to provide a unitary port 112. In a third exemplary embodiment illustrated in FIG. 5C, the pilot control port 116 is disposed adjacent to and in contact with the main gas port 117 to provide a unitary port 112. In such embodiment, the unitary port 112 has a lopsided figure-8 cross section.

Referring now to FIG. 6, there is illustrated an exemplary block diagram of a system, generally designated as 600, which is a simplified version of the gas sparing circuit 300, in accordance with an exemplary embodiment of the present invention. The block diagram 600 shows the gas sparing circuit 300 in terms of pressures. Further, the block diagram 600 in conjunction with FIG. 7A shows how a charged pilot control circuit 360 aids in system response. System response is plotted in FIG. 7A, which is described below.

In an exemplary embodiment, the pilot valve 330 requires a minimum threshold pressure $P_C$ to actuate and open the valve 330. It is to be understood that in any system, for a given circuit size, e.g., the size of the pilot control circuit 360, there will be a time value, t, for the full pressure in the system to build, i.e., for the gas sparing circuit 300 to activate, when the system is acted upon or, in the case herein, when the pilot control line 365 (pilot control circuit 360) is occluded.

The time t is affected by the total dead volume in the circuit 360. Thus minimizing the dead volume by controlling the interior diameter of the tubing in the circuit 360, the pliancy in the tubing material, and the length to the occluding part, e.g., the length from the flow reduction element 341 to the pilot air flow control switch 125, assists in reducing the time t. To reduce the time t to activation even further, a pilot control circuit 360 that not only utilizes the lowest dead volume available but also maintains a pressure as high as possible in the pilot control circuit 360, i.e., as close to the activation pressure of the valve 330 as possible, allows for almost immediate activation of the valve 330, thereby reducing the activation time t. Allowing a constant, albeit small, flow in the pilot control circuit 360 allows the gas sparing circuit 300 to maintain a pressure in the pilot control circuit 360 that is very close to the pressure $P_C$. Should the pilot control circuit 360 have no initial flow, the time required to equalize to the system inlet pressure, once flow is initiated and the circuit 360 occluded, would be significantly greater than the subject pilot control circuit 360 with constant flow.

Because there is a desire to minimize vented or lost gas in the main gas circuit 350, the flow rate in the pilot control circuit 360 is desirably minimized. Thus, the gas control unit 110, desirably includes a flow reduction element 341 which causes a small drop in pressure in the pilot control branch 320 to just below the threshold pressure $P_C$ of the valve 330 and which limits the flow rate in the pilot control circuit 360 when not occluded. A properly sized flow reduction element 341 in the pilot branch 320 provides both pressure drop and flow rate control when the pilot control circuit 360 is un-occluded and the gas in the pilot control circuit 360 is allowed to flow. When the pilot control circuit 360 is occluded and no flow occurs, i.e., when the pilot air flow control switch 125 occludes the vent port 351, there will be no pressure drop across the flow reduction element 341, and the pressure in the pilot control circuit 360 will rise quickly, because of the minimized circuit dead volume. The pressure in the pilot control circuit 360 equalizes with the pressure at the inlet 111 to actuate the valve 330.

In FIG. 6:

$P_1$=System inlet pressure (1)

$P_2$=Pressure just after the flow reduction element 341 at the pilot control input 333 of the gas sparing valve 330 (2)

$P_3$=Pressure in the pilot control line 365 proximal to the vent port 351 and at the end 122 of the main gas line 355 (3)

$P_C$=Pressure at the input 333 required to actuate the valve 330 (4)

For the simplified system 600 of FIG. 6, the following relationships hold true when the vent port 351 is open:

$P_2 < P_1$ (5)

$P_2 > P_3$, (6)

$P_2 < Pc \leq P_1$ (7)

By selecting the flow reduction element 341 and by reducing dead volume and pliancy (expandability of components) in the pilot control circuit 360, the pressure $P_2$ can be held very close to $P_C$, such that upon occlusion of the pilot circuit, $P_2$ quickly rises to the level of $P_1$, which is greater than $P_C$, and actuates the valve 330.

Pilot control is accomplished by occluding and venting the pilot control circuit 360, more specifically the control line 365. FIG. 3 illustrates that the gas sparing circuit 300 comprises a pilot air flow control switch 125. It is to be understood that the gas sparing circuit 300 is not limited to the element 125 being a switch. Any device to temporarily occlude the pilot control line 365 to actuate and open the gas sparing valve 330 is contemplated. The pilot control switch 125 operates in a normally open condition which holds the gas sparing valve 330 closed so that no gas flow occurs through the main gas branch 310 and the main gas line 355.

Illustrated in FIG. 7A is a graph of the pressures, $P_1$, $P_2$, and $P_3$ in the system 600, plotted over time as the pilot control circuit 360 is un-occluded, then is occluded, and then re-un-occluded. Illustrated in FIG. 7B is a graph of the main gas flow, designated as in the main gas line 355 and the pilot gas flow, designated as $V_2$, in the pilot control line 365, in accordance with an exemplary embodiment of the present invention. These graphs are now described with reference to occluding and un-occluding the pilot control line 365.

As illustrated, when the system 600 is in its initial state in which the pilot control circuit 360 is not occluded, the system inlet pressure $P_1$ remains relatively constant at a pressure $P_A$, the pressure in the line 305; pressure $P_2$ remains relatively constant at a pressure $P_B$, the residual, pre-charged pressure in (the original was better) the pilot control circuit 360; and pressure $P_3$ is constant at a pressure $P_{atm}$, atmospheric pressure, because the vent port 351 is open to atmosphere. Main gas flow $V_1$ is at 0 because the gas sparing valve 330 is closed. Pilot gas flow $V_2$ in the pilot control line 365 is at $V_P$, the un-occluded flow rate.

Pressure $P_2$ remains relatively constant at a pressure $P_B$ because the element 341 provides for a constant pressure drop from pressure $P_A$. As noted above, pressure $P_C$, which is illustrated in FIG. 6, is a constant, as it is the predetermined pressure required to actuate the valve 330. $P_C$ can be adjusted by altering the internal valve actuation spring and/or diaphragm in the valve 330.

Pressures $P_2$ and $P_3$ respond to occlusion and then un-occlusion in the pilot control circuit 360 (pilot control line 365). At time $t_1$, the pilot control circuit 360 is occluded, and pressure $P_2$ increases as the gas in the pilot control line 365 is no longer vented at the vent port 351. Pilot gas flow $V_2$ quickly reduces to zero because the pilot control line 365 is occluded. Pressure $P_2$ increases until equal to $P_C$ at time $t_2$, at which time the valve 330 is actuated and opens to allow the primary gas to flow through the main gas circuit 350 at the full inlet pressure $P_1$. The pilot gas flow $V_1$ begins to quickly increase from 0 to $V_M$, the un-occluded flow rate, at $t_2 + \Delta t$, where $\Delta t$ is a small elapsed time after $t_2$. The pressure $P_2$ continues to increase until it reaches the inlet pressure $P_1$ ($P_A$) at time $t_3$, at which time the pressure drop across the valve 330 is 0 psi. $P_2$ remains at $P_1$ ($P_A$) and $V_1$ remains at $V_m$ while the pilot control circuit 360 is occluded.

At time $t_4$, the pilot control circuit 360 is un-occluded and begins to vent. The pilot gas flow $V_2$ quickly increases to $V_P$. The pressure $P_2$ begins to decrease and continues to do so through time $t_3$, until it reaches $P_C$ at which time the valve 330 deactivates and closes, and the flow $V_1$ precipitously decreases to 0. The pressure $P_2$ continues to decrease until it settles back at its initial pressure $P_B$ at time $t_6$. When vented, the pressure $P_2$ drops enough to allow the main valve 330 to close but does not drop to atmospheric pressure $P_{atm}$ due to the residual constant flow in the pilot control circuit 360 and the length of the pilot control circuit 360.

Also illustrated in FIG. 7A is a plot of pressure $P_3$ at the vent port 351 and at the end 122 of the main gas line 355. The plot of $P_3$ is also approximately similar to the pressure after the flow reduction element 341 if the pilot control circuit 360 were held at atmospheric pressure. For purposes of the following discussion, the pressure $P_2$ just after the flow reduction element 341 in the pilot control circuit 360 when held at atmospheric pressure is designated as $P_2'$.

The plot of $P_3$ is now described with the understanding that $P_3$ is approximately the same as $P_2'$. Pressure $P_3$ is initially at atmospheric pressure, $P_{atm}$. At time $t_1$, the pilot control circuit 360 is occluded, and pressure $P_3$ increases as the gas in the pilot control line 365 is no longer vented at the vent port 351. Pressure $P_3$ increases until equal to the threshold pressure $P_C$ at time $t_7$. The pressure $P_3$ continues to increase until it reaches $P_1$ ($P_A$) at time $t_8$. $P_3$ remains at P ($P_A$) while the pilot control circuit 360 is occluded. At time, $t_4$, the pilot control circuit 360 is un-occluded and begins to vent, and the pressure $P_3$ begins to decrease and continues to do so through time $t_5$ when the valve 330 deactivates and closes. The pressure $P_3$ continues to decrease until it settles back at its initial pressure $P_{atm}$.

FIGS. 7A and 7B show that a pilot control circuit 360 which maintains a residual pressure $P_B$ higher than atmospheric pressure $P_{atm}$, will actuate the valve 330 and start the flow $V_1$ of main gas in the main gas circuit 350 more quickly than a system maintained at $P_{atm}$. The actuation time for the valve 330 for the system 300, 600 having a residual pressure $P_B$ in the pilot control circuit 360 higher than atmospheric pressure $P_{atm}$, is $t_2 - t_1$. The time for $V_1$ to go from 0 to $V_M$ is $t_2 + \Delta t - t_1$. The actuation time for the valve 330 if the system 300, 600 were to have a residual pressure $P_{atm}$ in the pilot control circuit 360 at the valve 330 would be $t_8 - t_1$. Exemplary values for $t_2+\Delta t-t_1$ and $t_8-t_1$ are 250 ms and 1250 ms, respectively. An exemplary value for $\Delta t$ is 25 ms. By maintaining the pilot control circuit 360 with pressure $P_2$ at a residual pressure $P_B$ rather than at $P_{atm}$ and by minimizing flow volume (dead volume) in the pilot control circuit 360, the time $t_2-t_1$ for pressure charging in the pilot control circuit 360 and for actuation of the valve 330 is minimized.

As discussed above, the pilot control branch 360 desirably causes quick response of the valve 330 to provide almost instantaneous flow to the patient after activation by the user. The pilot control circuit 360 also desirably uses minimal gas flow to actuate the valve 330 circuit and vent minimal gas to the environment when not activated. Conventional gas delivery circuits allow constant full, high-volume flow to the environment even when such gas is not being using by a patient. Such waste is not acceptable and is costly. The gas control unit 110 greatly reduces such waste.

In an exemplary embodiment, the reduced flow and quick response in the pilot control circuit 360 is accomplished by use of a small flow orifice in the element 341 to restrict and lower flow rate and volume in the pilot control circuit 360. Further, small bore tubing with minimal wall pliancy is used in the portions 320A-D of the pilot control branch 320 and in the pilot control line 365 to allow for a minimal flow area (cross section) and a minimal dead volume to provide for quick actuation of the gas sparing valve 330 when desired.

In addition, allowing a continuous small positive flow in the pilot control circuit 360 at all times minimizes the response time even further since, when occluded while having an initial positive flow, the pilot control circuit 360 is already almost fully charged with gas, as shown in FIG. 7A, and, thus, the internal flow $V_2+$ in the pilot control circuit 360 will be almost immediately directed into the gas sparing valve 330 upon occlusion, thereby building enough back pressure, quickly, to activate the gas sparing valve 330. In an exemplary embodiment, under such conditions, patient flow $V_1$ to a patient wearing the mask 130 is initiated in fewer than 500 milliseconds. In another exemplary embodiment, patient flow $V_1$ is initiated in about 250 milliseconds or less.

As shown in FIGS. 7A and 7B, by maintaining the pilot control circuit 360 fully charged or nearly fully charged, response time is reduced compared to conventional systems. Should the pilot control circuit 360 be evacuated with no positive pressure or flow, the circuit 360 would be at atmospheric pressure $P_{atm}$ and would require time to fill and fully charge once flow was applied and the circuit 360 occluded. This charge time significantly delays system activation and renders use of the system 100 not desirable. Since the gas sparing valve 330 requires a minimum threshold pressure $P_C$ to activate, the closer the pilot control circuit 360 is maintained to this minimum threshold pressure $P_C$, the quicker activation of the valve 330 occurs when the pilot circuit 330 is occluded and the full pilot pressure $P_A$ reached.

Separate gas sources for the main gas circuit 350 and the pilot control circuit 360 are not practical in a modular portable system with minimal complexity. Thus, the system 300 is designed so that the pilot control gas, the gas within the pilot control circuit 360, is sourced from the same place as the system gas (also referred to herein as the "primary gas" or "patient gas"), the gas within the main gas circuit 350 (also referred to herein as the "primary gas circuit 350").

Because the system 300 uses a common gas source for both the primary and pilot gas flow, means to stop the loss of pilot gas flow and pressure upon activating the gas sparing valve 330, until desired by the operator, is desirably implemented. Should no means be provided to maintain the required pressure in the pilot control circuit 360 to hold the main valve 330 open, the main valve 330 may begin to oscillate between an open and closed position as the pressure $P_2$ in the pilot control branch 320 fluctuates down and then up as the main valve 330 opens and then closes, respectively. This may result in gas flow in the main gas line 355 oscillating between flow and no flow in a manner not desired by the operator.

To reduce or eliminate oscillation of the valve 330, the system 300 comprises a check valve 340, which is designed to eliminate backflow in the pilot branch 320 if there is a shift in the pressure differential across the element 341 when the gas sparing valve 330 opens, this shift in pressure differential would reverse the flow direction of gas in the pilot branch 320. The check valve 340 is used to lock and maintain pressure in the pilot branch 320 once a pressure level has been established assuming no gas is then allowed to escape from the opposite end of the branch 320, i.e., via the vent port 351. Thus, by placing a check valve in the pilot control circuit 360 before the flow reduction element 341, when the outlet switch/valve 125 is occluded by the operator and the pilot control circuit 360 is pressurized, any drop in pressure on the inlet side of the check valve 340, which may occur upon the main valve 330 opening, will not cause a pressure drop in the pilot control circuit 360. Thus, the main valve 330 remains open and does not oscillate between open and closed. Without the check valve 340, any undesired (uncontrolled) loss of pressure in the main gas circuit 350 might cause the main valve 330 to close prematurely in an uncontrolled manner or to oscillate between open and closed due to pressure fluctuations in the pilot control circuit 360. Both premature closing of the main valve 330 and uncontrolled oscillation of the main valve 330 between open and closed are undesirable.

Figure 8A:
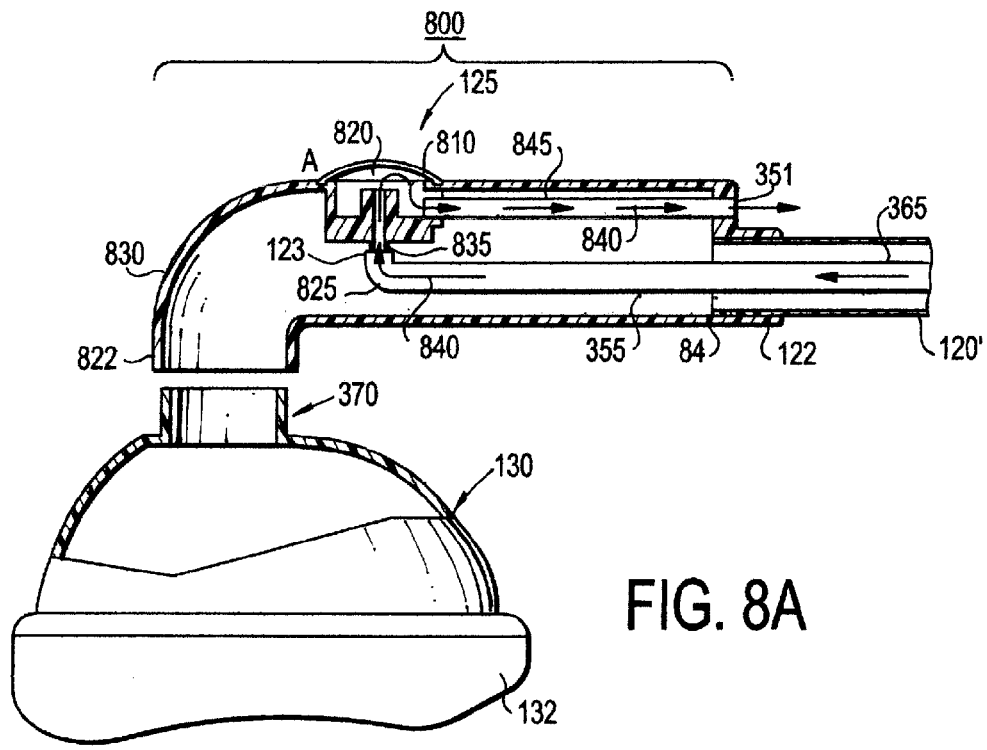
FIGS. 8A and 8B illustrate exemplary operation of an exemplary embodiment of a pilot control switch used to selectively occlude the pilot control branches of FIGS. 1 and 2, in accordance with an exemplary embodiment of the present invention.
Figure 8B:
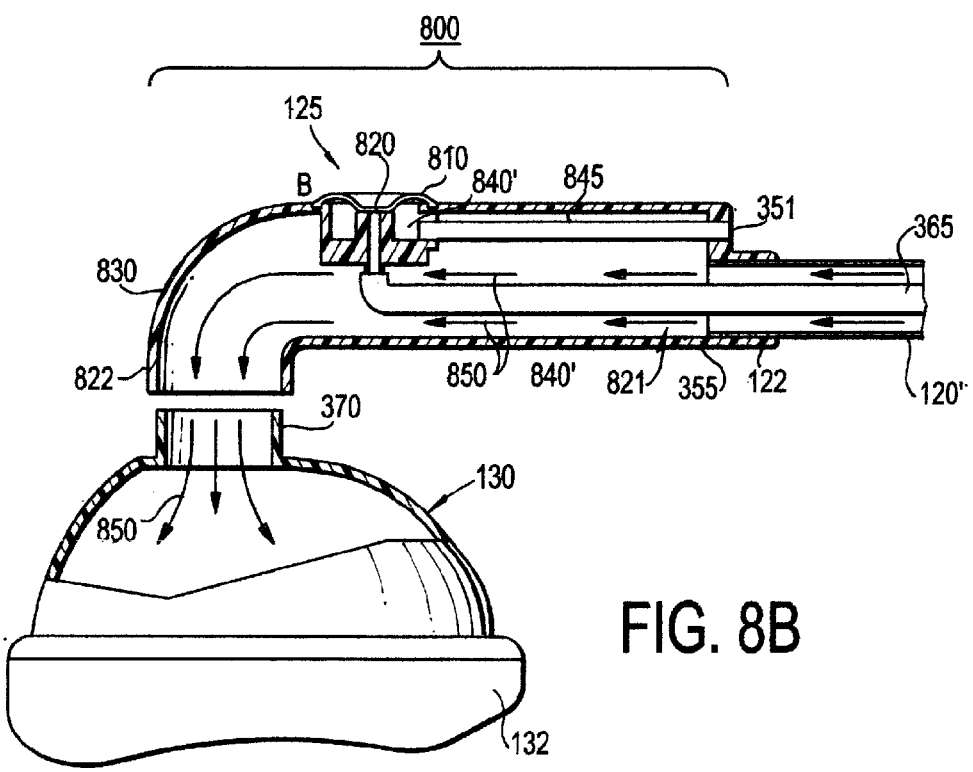

Referring now to FIGS. 8A and 8B together, there is illustrated operation of an exemplary embodiment of the pilot air flow control switch 125 disposed within a handle 800, in accordance with an exemplary embodiment of the present invention. FIG. 8A illustrates the switch 125 in an open position A. FIG. 8B illustrates the switch 125 in a closed position B. As illustrated in FIGS. 8A and 8B, the handle 800 is connected to a second end 122 of an exemplary embodiment of the disposable breathing circuit 120, generally designated as 120' in FIGS. 8A and 8B. The handle 800 may be permanently or removably attached to the disposable breathing circuit 120. FIG. 8C illustrates various views of an exemplary embodiment of the disposable breathing circuit 120', in accordance with an exemplary embodiment of the present invention.

The disposable breathing circuit 120' illustrated in FIGS. 8A-8C differs from the disposable breathing circuit 120 because the disposable breathing circuit 120' does not include the switch 125 or the vent 351. Instead, those components are disposed within the handle 800 illustrated in FIGS. 8A and 8B. Thus, the main gas line 355 extends through the disposable breathing circuit 120' from the first end 121 to the second end 122, which second end 122 is connected to a first end 821 of the handle 800. The pilot gas line 365 extends through the disposable breathing circuit 120' from near the first end 121 to near the second end 122, as seen best in FIG. 8C.

In the embodiment of the handle 800 illustrated in FIGS. 8A and 8B, the pilot air flow control switch 125 is a pliant membrane 810 disposed over a pilot control orifice 820. The switch 125 and specifically the pliant membrane 810, when in position A, does not occlude the pilot control orifice 820 and when in position B, does occlude the orifice 820. In an alternative embodiment, a rigid flow switch could replace the pliant member 810 and perform the same function.

The handle 800 allows the user to hold the mask 130 against the patient's mouth and nose. The handle 800 comprises a bend 830 and an end 822 to which the mask 130 is attached. At the second end 123 of the pilot control line 365, the pilot control line 365 comprises a bend 825, which connects the pilot control line 365 to a riser or port 835 which opens to atmosphere at the pilot control orifice 820.

As illustrated in FIG. 8A, when the pilot air flow control switch 125 is in the open position A, pilot gas 840 flows through the pilot control line 365, around the bend 825, up the riser or port 835, and through the pilot control orifice 820. The pilot gas 840 then passes through an exhaust port 845 and is exhausted through the vent port 351. Because pilot gas 840 is vented through the vent port 351, the gas sparing valve 330 is deactivated and does not allow main gas 850 to flow through the main gas line 355.

As illustrated in FIG. 8B, when the pilot air flow control switch 125 is in the closed position B, i.e., when the pliant member 810 is depressed, the pilot control orifice 820 is occluded by the membrane 810, and pilot gas 840 is not vented through the vent port 351. The lack of pilot gas flow is labeled as 840' in FIG. 8B. Because there is no pilot gas flow 840', the gas sparing valve 300 is actuated and main gas 850 flows through the main gas line 355, out the second end 822 of the handle 800, and through the mask 130. Upon release of the pliant member 810, the pilot gas 840 vents, de-actuating and closing the gas sparing valve 330 and stopping flow of the main gas 850 to the patient mask 130.

FIGS. 8A-8C illustrate that the pilot control line 365 is extended through the breathing circuit 120' to the end 122 (or near to the end 122) of the breathing circuit 120, and the handle 830 is attached to the end of the breathing circuit 120. It is to be understood that in an exemplary embodiment, the breathing circuit 120 may be modified so that the handle 830 is disposed at the end 122 of the breathing circuit 120.

Figure 2:
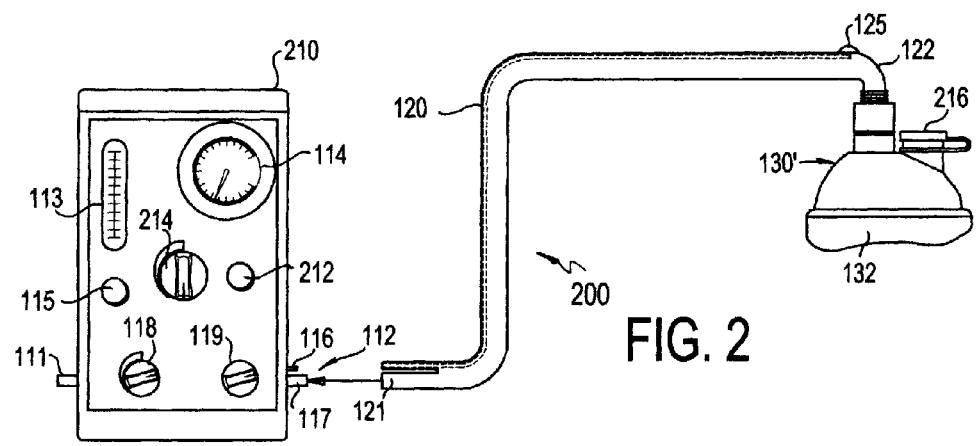
FIG. 2 illustrates an exemplary embodiment of an alternative system for delivering gas to a patient, the alternative system comprising a gas control unit, a disposable breathing circuit, and a mask, the gas control unit comprising a gas sparing circuit comprising a primary branch, a pilot control branch, and a continuous positive airway pressure (CPAP) branch, the primary branch comprising a gas sparing valve, in accordance with an exemplary embodiment of the present invention.

Referring now to FIG. 2, there is illustrated a block diagram of an alternative system, generally designated as 200, for delivering gas to a patient via an alternative embodiment of the patient mask 130, generally designated in FIG. 2 as 130', in accordance with an exemplary embodiment of the present invention. The system 200 comprises all of the elements of the system 100, except for the patient mask 130, but additionally includes functionality for a second gas delivery mode, as described below, namely in a continuous positive airway pressure (CPAP) gas delivery mode where a continuous low pressure, low flow-rate gas is required after resuscitation.

The system 200 comprises a gas control unit 210, rather than the gas control unit 110. The gas control unit 210 comprises the elements 111-119, though used in the system 200 capable of a CPAP gas delivery mode, as is now described. Accordingly, the gas control unit 210 additionally comprises a CPAP flow rate control 212 to allow the user to select a desired CPAP flow rate and a mode-selection switch 214 for selection between the CPAP mode and the gas-sparing resuscitation mode of the system 100.

The mask 130' used with the system 200 differs from the mask 130 used with the system 100. The mask 130' incorporates a CPAP exhalation port 216, which allows the user of the mask 130' to exhale when the system 200 is operating in the CPAP gas delivery mode. The mask 130' is described in more detail below with respect to FIG. 17.

Figure 21:
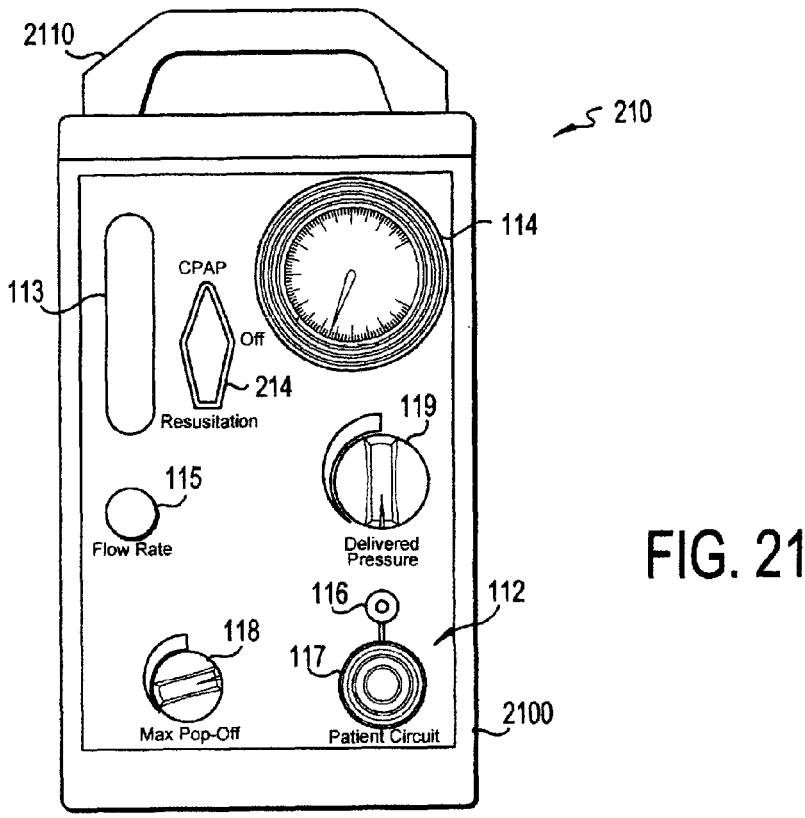
FIG. 21 illustrates a view of an exemplary housing for the gas control unit of FIG. 2, in accordance with an exemplary embodiment of the present invention.

An exemplary view of the external of the gas control unit 210 is illustrated in FIG. 21, in accordance with an exemplary embodiment of the present invention. The various components of the gas control unit 210 illustrated in FIG. 2 and described above are mounted to an enclosure 2100 of the gas control unit 210. Attached to the enclosure 2100 is a handle 2110 for carrying the gas control unit 210.

Figure 4:
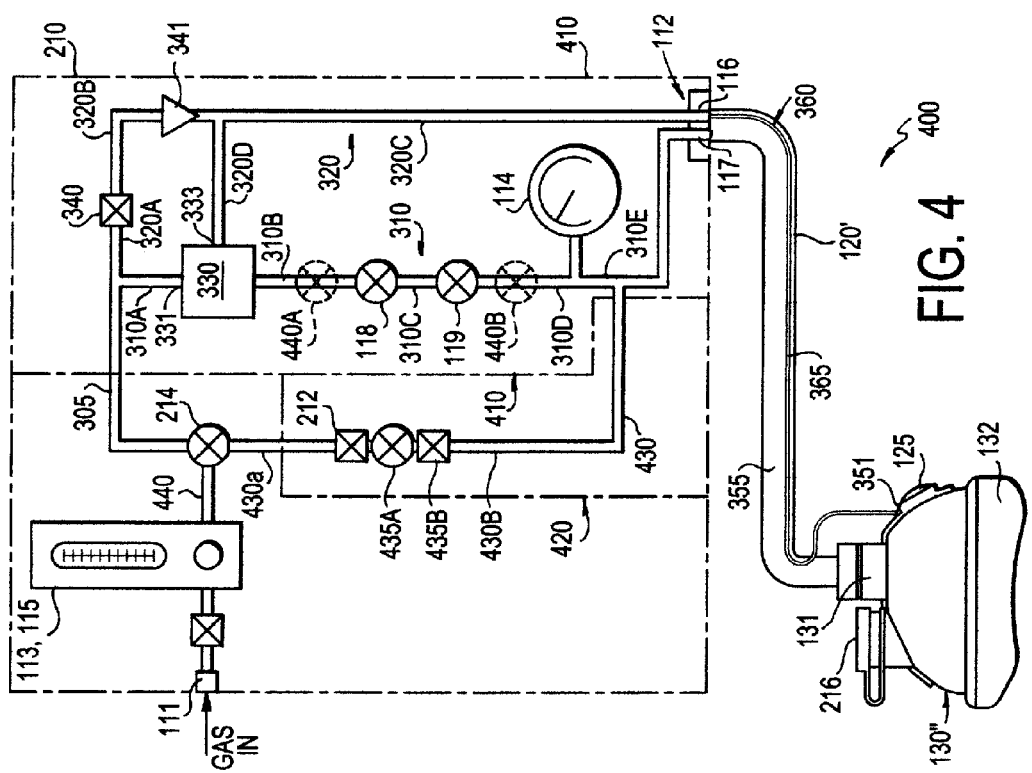
FIG. 4 illustrates an exemplary block diagram of the exemplary embodiment of the system of FIG. 2, in accordance with an exemplary embodiment of the present invention.

Referring now to FIG. 4, there is illustrated a block diagram of a gas sparing circuit 400 comprising the gas control unit 210, an embodiment of the disposable breathing circuit 120, generally designated in FIG. 4 as 120', and an alternative embodiment of the patient mask 130', generally designated in FIG. 4 as 130", in accordance with an exemplary embodiment of the present invention. The gas sparing circuit 400 uses all of the components illustrated in FIG. 2 and additional components, as illustrated in FIG. 4. The gas sparing circuit 400 incorporates the primary branch 310 and the pilot control branch 320 of the gas sparing circuit 300 in the resuscitation side 410 of the gas sparing circuit 400. The gas control unit 210 additionally comprises a CPAP circuit or branch 430 in a CPAP side 420 of the gas sparing circuit 400. The CPAP circuit or branch 430 comprises portions or lines 430A-430B. The CPAP circuit or branch 430 is a continuous flow circuit when in use as there is no gas sparing control on this side.

The resuscitation side 410 comprises the primary branch 310 and the pilot control branch 320 of the gas sparing circuit 300, which branches operate similarly in the gas sparing circuit 400 to those in the gas sparing circuit 300. The primary branch 310 and the pilot control branch 320, however, are modified slightly for use in the gas sparing circuit. First, the portions 310A and 320A are not directly connected to the flow meter 113 with flow control 115 via the inlet line 305, as they are in the gas sparing circuit 300. Instead, the inlet line 305 is directly connected to the mode-selection switch 214. Second, the portion 310e of the primary branch 310 in the gas sparing circuit 400, while still directly connected to the main air port 117, is also connected to the portion 430B of the CPAP branch 430. Third, the primary branch 310 may include a check valve 440A in the portion 310B or a check valve 440B in the portion 310D to further restrict back flow into the resuscitation side 410 when the gas sparing circuit 400 is operating in CPAP mode.

The CPAP branch 430 comprises the portion 430A, which couples the mode-selection switch 214 to the CPAP flow control valve 212 as needed. The portion 430B couples the CPAP flow control valve 212 to the portion 310E of the primary branch 310. The mode-selection switch 214 is coupled to the flow meter 113 and flow control 115 via a portion 440. The mode-selection switch 214 allows the operator to select for CPAP continuous air delivery (CPAP mode) through the primary gas line 355 via the CPAP branch 430 or to select for pilot-controlled primary gas delivery (resuscitation mode) through the primary gas line 355 via the resuscitation side 410, and the flow control valve 212 allows the operator to select the rate of gas flow in the CPAP branch 430.

In an exemplary embodiment, the portion 430B includes a pressure relief valve 435A and/or a check valve 435B. The pressure relief valve 435A provides venting for overpressure in the CPAP branch 430, and the check valve 435B prevents backflow in the CPAP branch 430. In another exemplary embodiment, CPAP Branch portion 430B could be connected to Main branch portion 310B allowing the pressure relief valve 118 to be disposed downstream of the connection with the portion 430B. In such embodiment, the pressure relief valve 118 provides venting for overpressure in either the CPAP branch 430 or the primary branch 310.

Separate flow control valves in the CPAP branch 430 and the main gas branch 310 are contemplated. These valves are, respectively, the flow control valves 212 and 115. In an exemplary alternative embodiment, the flow control valve 212 is removed, and the flow control valve 115 is used to regulate the rate of gas flow in the main gas branch 310 and the CPAP branch 430. In another exemplary alternative embodiment, the flow control valve 115 is disposed in the portion 310A downstream of the mode-selection switch 214 to control flow in the primary branch 310, and the flow control valve 212 is disposed in the CPAP branch 430 to control CPAP flow. In yet another exemplary alternative embodiment, check valves 440A and/or 440B are contemplated to stop backflow in the primary branch 310. The check valves 435B, 440A, and 440B also prevent cross flow between the CPAP branch 430 and the primary branch 310.

The mask 130" differs from the mask 130' because the mask 130' includes the switch 125 and the vent 351, respectively designated as 125' and 351' in FIG. 4. It is to be understood that the mask 130" incorporates the CPAP exhalation port 216 used in the mask 130'. This port is open when in CPAP mode but is closed when in resuscitation mode. In an exemplary alternative embodiment, the disposable breathing circuit 120 and the mask 130' are used with the gas sparing circuit 400. In another exemplary alternative embodiment, the handle 800 may be attached to the disposable breathing circuit 120' and the mask 130' if used with the gas sparing circuit 400 or may be incorporated into the mask 130" if used with the gas sparing circuit 400.

Figure 9:
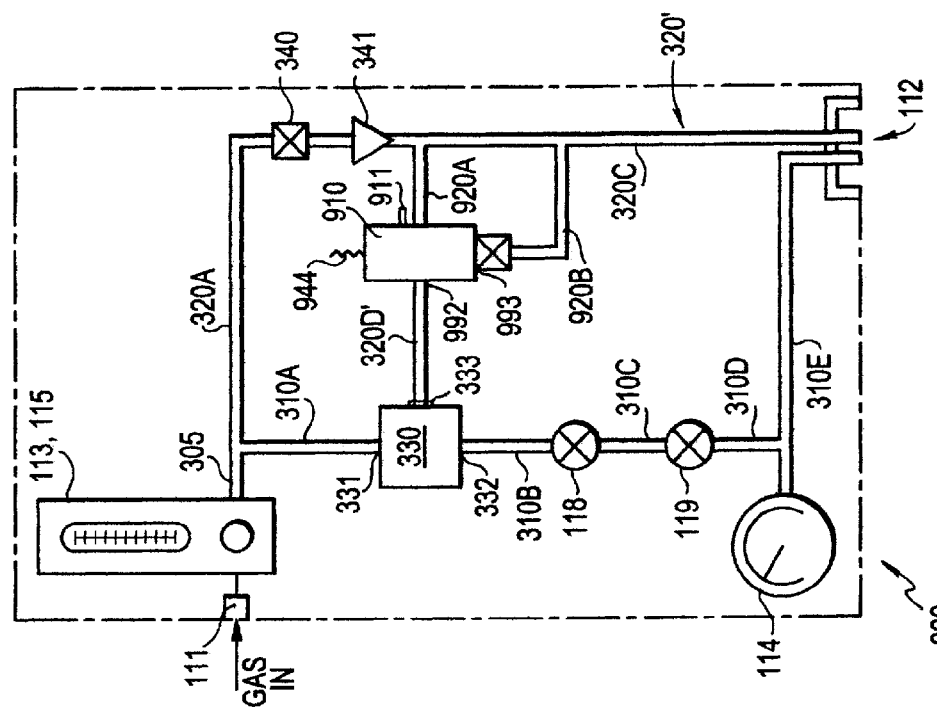
FIG. 9 illustrates an exemplary embodiment of a gas sparing circuit comprising a timer control for main-flow on-time control, in accordance with an exemplary embodiment of the present invention.

Referring now to FIG. 9, there is illustrated an exemplary alternative embodiment of the gas sparing circuit 300, generally designated in FIG. 9 as 900, in accordance with an exemplary embodiment of the present invention. The gas sparing circuit 900 uses all of the components illustrated in FIG. 3, modified as described below, and additional components, as illustrated in FIG. 9. The gas sparing circuit 900 incorporates the main gas branch 310 and the pilot control branch 320, as modified as a pilot control branch 320'. In another exemplary embodiment, a CPAP branch, such as the CPAP branch 430 of FIG. 4, could also be added to the gas sparing circuit 900 to add CPAP functionality.

The pilot control branch 320' comprises the elements of the pilot control branch 320 of the pilot control branch 320 and additionally a pneumatic timer control 910 configured to control the on-time of the main gas sparing valve 330. The portion 310D of the pilot control branch 320 is replaced by portions 320D' and 920A and 920B. If used to control the on-time of the main gas sparing valve 330, the pneumatic timer control 910 is a normally open valve.

The portion 320D' couples an output 992 the pneumatic timer control 910 to the control side 333 of the gas sparing valve 330. The portion 920A couples the portion 320C to an input 911 of the pneumatic timer control 910. The portion 920B couples the portion 320C to a timer unit 993.

Operation of the gas sparing circuit 900, with on-time control, is now described. Operation begins with the pilot control circuit 360 in an un-occluded state, the gas sparing valve 330 closed, and pilot gas at pressure $P_B$ is applied to the control side 333 of the gas sparing valve 330 through the pneumatic timer control 910, which is in an open state. Upon closure or occlusion of the pilot control line 365, the gas sparing valve 330 opens, as described above with respect to FIGS. 3, 6, and 7, and pressure at the timer unit 993 increases. When the pressure at the time unit 993 reaches a threshold pressure, a counter within the timer unit 993 starts and counts until it reaches an activation time. After the activation time of the timer 993 is reached, the timer 993 cycles and closes a valve in the pneumatic timer 910 and vents the pilot connection 320D' of the gas sparing valve 330 via a vent 994, thereby causing the gas sparing value 330 to close and main flow through the main gas line 355 to stop. The cycle may repeat after the pilot control line 365 is vented, which causes the timer unit 993 to reset. In this modality, the provision of primary gas through the gas sparing valve 330 for each breath is triggered by the user occluding the pilot control line 365. Thus, re-occlusion of the pilot control line 365 starts each resuscitation breath. Also, in this modality, the user could deliver inhalation breaths in succession without allowing for complete exhalation, if desired, since any venting of the pilot line would reset the timer valve 993 and allow the cycle to restart very quickly. Exhalation is accomplished as described herein, such as via exhaust ports in the mask 130 or 130' or via exhaust ports in a hand piece to which the mask 130 or 130' is connected, such as the exhaust ports 1226 in the hand piece 1200 described below.

In this way, the gas sparing circuit 900 controls the amount of time gas is provided via the main gas line 355 and thereby controls the inhalation time of the patient using the gas sparing circuit 900. The activation time can be adjusted from fractions of a second to several seconds as desired by the user. The user may set the activation (breath) time of the timer unit 993 to be between 0.5 to 3 seconds. Desirable breath time is approximately 1.0 to 1.5 second for inhalation breath flow followed by 1.0 to 3.0 seconds of vent or exhalation time.

Figure 10:
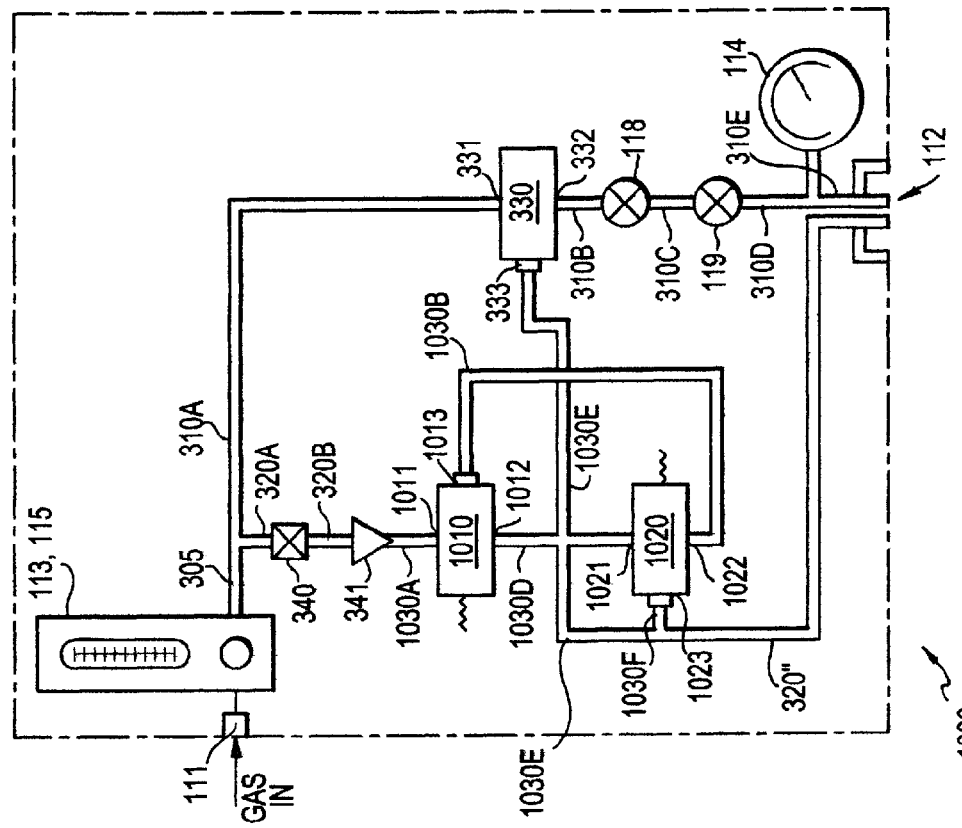
FIG. 10 illustrates another exemplary embodiment of a gas sparing circuit comprising a timer control for main-flow on-time and off-time control, in accordance with an exemplary embodiment of the present invention.

Should the user desire automatic continuous control of the inhalation time followed by automatic control of the exhalation time, two pneumatic timers could be used in an exemplary embodiment of the gas sparing circuit 900, generally designated as 1000 in FIG. 10, in accordance with an exemplary embodiment of the present invention. The gas sparing circuit 1000 uses all of the components illustrated in FIG. 3, modified as described below, and additional components, as illustrated in FIG. 10. The gas sparing circuit 1000 incorporates the primary branch 310 and the pilot control branch 320', as modified as a pilot control branch 320". In another exemplary embodiment, a CPAP branch, such as the CPAP branch 430 of FIG. 4, could also be added to the gas sparing circuit 1000 to add CPAP functionality.

The pilot control branch 320" comprises the elements of the pilot control branch 320' of the gas sparing circuit 900 and additionally two pneumatic timer controls 1010 and 1020. In this configuration, the first timer control 1010 controls the on (inhalation) time (the time during which the gas sparing valve 330 is open) and the second timer control 1020 controls the off (exhalation) time (the time during which the gas sparing valve 330 is closed).

In the pilot control branch 320", the element 341 is coupled to an inlet 1011 of the first timer 1010 via a portion 1030A. An outlet 1012 of the first timer control 1010 is coupled to an inlet 1021 of the second timer control 1020 via portion 1030D. An outlet 1022 of the second timer control 1020 is coupled to a timer 1013 of the first timer control 1010 via a portion 1030B.

The control side 333 of the gas sparing valve 330 is coupled to the outlet 1012 and the inlet 1021 via a portion 1030E which also connects to the outlet port 112. The portion 1030E is also coupled to a timer 1023 of the first timer control 1020 via a portion 1030F.

Operation of the gas sparing circuit 1000 is now described. Operation begins with the pilot control circuit 360 in an un-occluded state, the gas sparing valve 330 closed, and pilot gas at pressure $P_B$ is applied to the control side 333 of the gas sparing valve 330 through the pneumatic timer control 1010, which is in an open state. The pneumatic timer control 1020 is in a closed state, and the line 1030B has been vented. Upon closure or occlusion of the pilot control line 365, the gas sparing valve 330 opens, as described above with respect to FIGS. 3, 6, and 7, and primary gas is provided to the patient via the primary circuit 350. At the same time, pressure at the timer unit 1023 increases. When (almost instantaneously) the pressure at the timer unit 1023 reaches a threshold pressure, a valve within the pneumatic timer control 1020 closes and a counter within the timer unit 1023 starts. When the counter within the timer unit 1023 reaches an activation time, the timer 1023 cycles a valve in the pneumatic timer control 1020 to an open state and vents the pilot circuit 360.

Because the valve in the pneumatic timer control 1020 is opened, pilot gas is allowed to pass from the inlet 1021 to the outlet 1022 and to the timer 1013 of the pneumatic timer control 1010 via the line 1030B. Pressure at the timer unit 1013 increases. When (almost instantaneously) the pressure at the timer unit 1013 reaches a threshold pressure, a valve within the pneumatic timer control 1010 closes, thereby shutting down flow of the pilot gas from the inlet 1011 to the outlet 1012 of the pneumatic timer control 1010. Because the pneumatic timer control 1020 is in an open state and is venting the pilot circuit 360, the gas sparing valve 330 closes. This stops the flow of gas to the patient and allows exhalation to occur. This discontinuation of pilot flow also resets timer 1020.

A counter within the timer unit 1013 starts and counts until it reaches an activation time. After the activation time of the timer 1013 is reached, the timer 1013 cycles the valve in the pneumatic timer 1010 to an open state to restart the flow of pilot gas from the inlet 1011 to the outlet 1012, which applies pilot gas to the pneumatic timer control 1020 to close the valve therein. At the same time, the gas sparing valve 330 opens, and primary gas is again provided to the patient via the primary circuit 350. Once the exhalation cycle is started, i.e. when the valve in the pneumatic timer 1010 closes, the user cannot deliver another inhalation breath until the exhalation cycle is fully completed. This ensures a full exhalation cycle is completed.

Operation of the gas sparing circuit 1000 cycles through the above-described process as long at the pilot air flow control switch 125 is closed. When the user releases the switch 125, the cycle stops. Additionally a mechanical or electrical latch or closure device can be added to the gas sparing circuit 1000, at the pilot control switch 125, that would allow for mechanical latching (closure) of the switch 125 in the closed position thus allowing for continued ventilation of the patient where the user would not have to hold the switch 125 in the closed position with his or her hand. This latch could be switched in and out to hold the pilot control switch 125 in the closed position or allow it to be in the open position for manual, finger-based activation.

In this configuration, once the pilot control line 365 is occluded, the system 1000 automatically cycles between inhalation (gas sparing valve 330 open to provide gas in the main gas line 355), and exhalation (gas sparing valve 330 closed). The user may set the ventilation breath time by setting the activation time of the timer unit 1023 to be between 0.5 to 3 seconds. Desirable breath time is approximately 1.0 to 1.5 second for inhalation breath flow. The user may set the exhalation time by setting the activation time of the timer unit 1013. Desirable exhalation time is approximately 1.0 to 3.0 seconds for exhalation breath flow.

Although FIGS. 9 and 10 illustrate using pneumatic time controls, other embodiments using electro-pneumatic controls or timer-based triggers are contemplated. In a gas-sparing circuit incorporating a timer-based trigger, the user activates the trigger to occlude the pilot control line 365 and activate the gas sparing valve 330. Then, within the trigger, a mechanical, electrical, or pneumatic-mechanical switch cycles over the desired time period and opens the pilot control line 365 to atmosphere, thereby closing the gas sparing valve 330, stopping primary airflow.

Figure 11A:
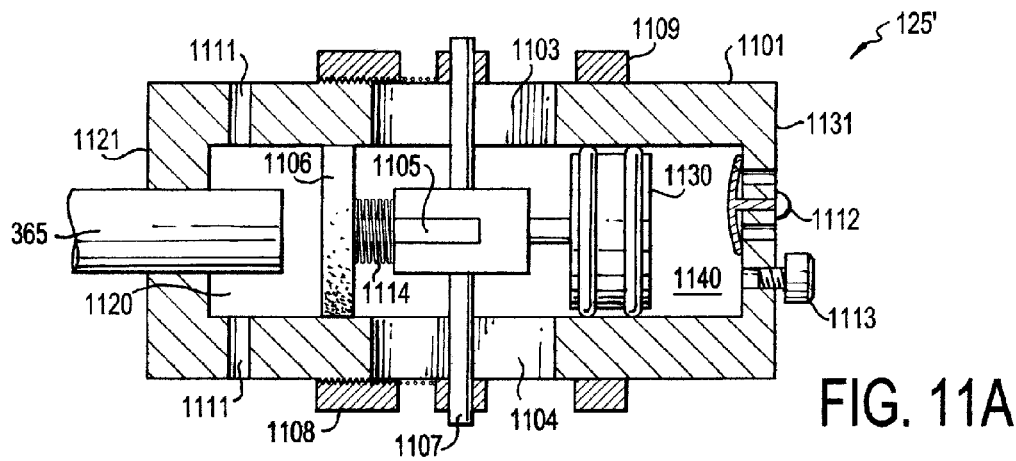
FIGS. 11A and 11B illustrate exemplary views of an exemplary embodiment of a timer-based trigger used to selectively occlude the pilot control branches of FIGS. 1 and 2, the timer-based trigger providing main-flow on-time control, in accordance with an exemplary embodiment of the present invention.
Figure 11B:
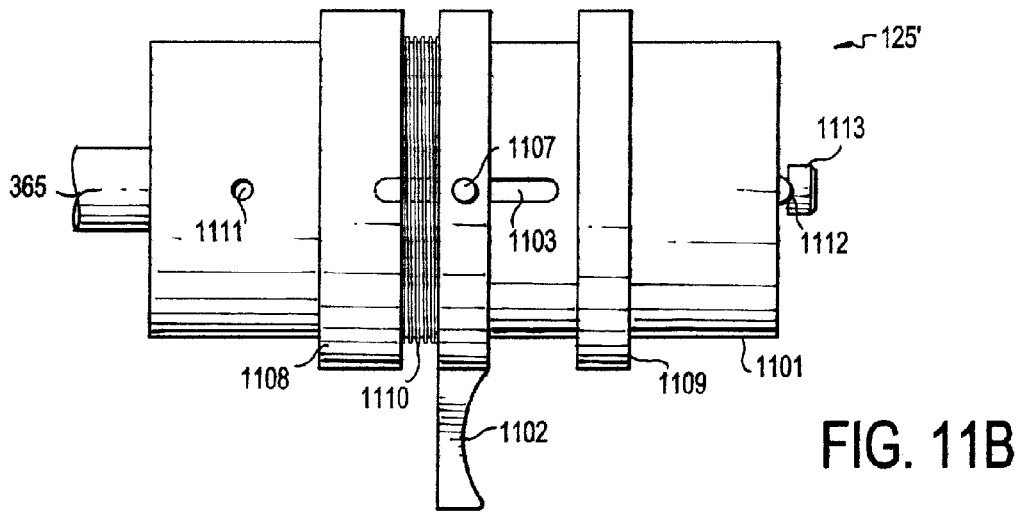

Referring now to FIG. 11A, there is illustrated a side cross-sectional view of an exemplary embodiment of a pneumatic-mechanical timer-based trigger 125' and to FIG. 11B, there is illustrated a top view revealing internal details of the trigger 125', in accordance with an exemplary embodiment of the present invention. The trigger 125' may be substituted into the gas sparing circuits 300 and 400 to replace the trigger 125.

The trigger 125' comprises a housing 1101 in which a trigger handle 1102 is slidably disposed. The trigger handle 1102 is connected to a guide rod 1107 which passes through slots 1103 and 1104 in the housing. The guide rode 1107 may slide from one end of the slots 1103 and 1104 to the other as the trigger handle 1102 slides within the housing 1101. The trigger handle 1102 is coupled to a plunger which terminates in a soft diaphragm 1106. Disposed on the plunger between the trigger handle 1102 and the diaphragm 1106 is a spring 1114.

The pilot control line 365 pierces a first end 1121 of the housing 1101 and terminates within an interior space 1120 of the housing 1101 formed between the housing 1101 and the diaphragm 1106. The interior space 1120 vents to the outside of the housing 1101 via vents 1111. Disposed at a second end 1131 of the housing 1101 is a plunger 1130, which is attached to the trigger handle 1102. The housing 1101 forms an interior space 1140 between the plunger 1130 and the second end 1131 of the housing 1101. The interior space 1140 vents to the outside of the housing 1101 via a one-way diaphragm valve 1112. Also disposed in the housing 1101 at the second end 1131 is a vent valve 1113, which is used to set vent time.

Disposed on the housing of the housing 1101 is a timer adjuster nut 1108 for adjusting the timer. Disposed around the housing 1101 between the nut 1108 and the trigger handle 1102 is a spring 1110. A stop 1109 provides a stop for lateral movement of the trigger handle 1102.

Operation of the trigger 125' is now described. The user pulls the trigger 125' toward the first end 1121, thereby pushing the soft diaphragm 1106 against the end of the pilot control line 365 and compressing the spring 1114 between the diaphragm 1106 and the trigger handle 1102. The spring 1114 provides for tactile feeling in the trigger 125'. Once the pilot control line 365 is occluded, the gas sparing valve 330 opens allowing primary flow.

When the trigger handle 1102 is pulled, in addition to advancing the soft diaphragm 1106, the trigger handle 1102 pulls the plunger 1130 away from the second end of the housing 1101. As the trigger handle 1102 and plunger 1130 advance, the chamber fills 1140 with air via the one way diaphragm valve 1112. When the trigger handle 1102 is released either by the user or by design via an automatically disengaging trigger activator, the spring 1110 applies force on the trigger handle 1102 to move the plunger 1130 back to its initial position. Since the chamber 1140 is now filled with air, the pressure in the chamber 1140 resists movement of the plunger 1130. Air from the chamber 1140 vents with movement of the plunger 1130. The adjustable vent valve 1113 allows the rate of the venting of the chamber 1140 to be controlled.

As the air in the chamber 1140 vents through the vent valve 1113, the plunger 1105 moves toward its original position and the pressure of the spring 1114 on the soft diaphragm 1106 begins to reduce. When the plunger 1105 has travelled a sufficient distance, the force of the spring 1114 on the diaphragm 1106 will be low enough such that the pressure in the pilot control line 365, which is 50 psi, will create enough force on the rear surface of the soft diaphragm 1106 to force the diaphragm 1106 open. The pilot control line 365 vents through the chamber 1120 and the vents 1111 to the outside of the housing 1101. As the pressure in the pilot control line 365 reduces past pressure $P_C$, the gas sparing valve 330 closes and air flow in the main gas line 355 stops. The spring 1110 pushes the trigger handle 1102 laterally until the trigger handle 1102 comes into contact with the stop 1109, at which time the plunger 1130 stops moving.

Thus, a timer circuit is created by the timer-based trigger 125'. The time duration of air flow through the main gas line 355 is controlled by the return travel distance of the trigger handle 1102 and the speed of the plunger 1130. Adjustment of the nut 1108 adjusts travel of the trigger handle 1102 to allow adjustment of the timer circuit of the timer-based trigger 125'. Further, the vent time of the chamber 1140 is adjustable by the vent valve 1113 to further provide for adjustment of the timer circuit of the timer-based trigger 125'.

A patient using the CPAP system 200 may attempt to breathe in an amount of air that is larger than baseline air flow provided by the CPAP side 420 of the system 200. Under these conditions, a means is desirably provided to allow for this larger air quantity to enter the system 200.

In conventional CPAP systems, the masks have special valves that allow for this larger air quantity. Although use of a special mask is possible in the CPAP system 200, it is not optimal. In addition, if spontaneous breathing were to occur during normal resuscitation where a CPAP mask in a conventional CPAP system cannot be used, the patient would not be able to draw in the extra air desired.

In conventional bag and mask systems, a valve within the rear of the bag system allows for air flow should the patient begin to breathe. However, these devices cannot provide CPAP functionality, and they have no flow and pressure controls. In the system 200 or 400 described above, because such systems are closed or could be very remote from the patient, a valve in the system that would allow for spontaneous breathing would be ineffective because the breathing circuit 120 would be too long to allow for minimal flow restriction. Thus, in order to minimize the restriction to a spontaneous breath with the system 200 or 400, it is desirable to provide a spontaneous breath valve system as close to the patient as possible. However, this valve desirably remains closed during resuscitation and CPAP positive air flow and only opens when an air flow, larger than the resuscitation or CPAP flow, is demanded by the patient via inhalation breath volume.

Figure 12:
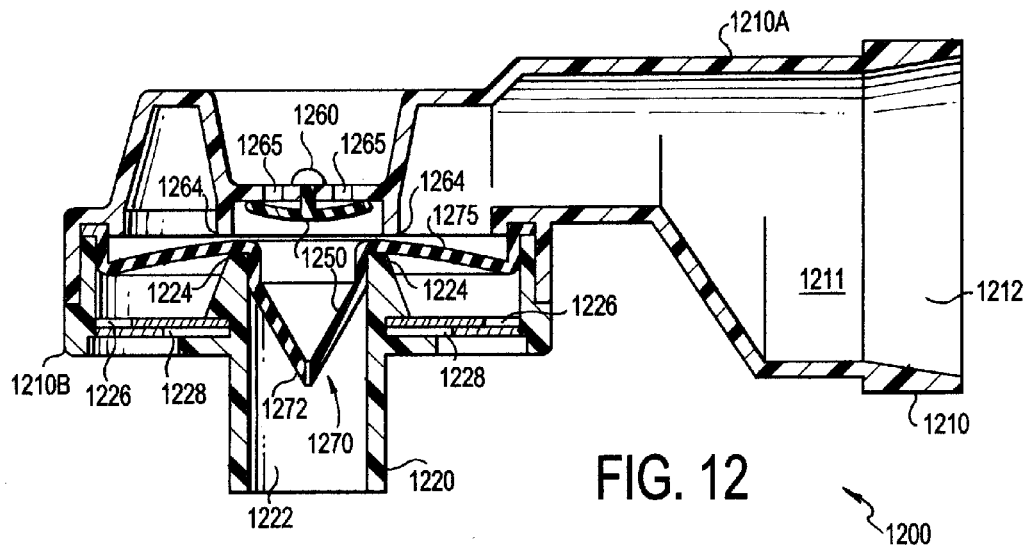
FIG. 12 illustrates an exemplary embodiment of a mask connection for use with a gas sparing circuit, the mask connection comprising a spontaneous breath valve, in accordance with an exemplary embodiment of the present invention.

Referring now to FIG. 12, there is illustrated an exemplary embodiment of the mask connection 370, generally designated as 1200 in FIG. 12, in use with a valve system 1250 to accommodate a patient's ability to draw in extra air if desired, in accordance with an exemplary embodiment of the present invention. The mask connection 1200 comprises a housing 1210, a rotating outlet port 1220, and the valve system 1250. The housing 1210 comprises, at a first end 1212, a gas inlet 1211, which is connected to the second end 122 of the disposable breathing circuit 120, and, at a second end 1220, an outlet 1222, which is connected to the mask 130. In an exemplary embodiment, the housing 1210 is a two-piece housing comprising a first portion 1210A and a second portion 1210B. The valve system 1250 allows the same mask 130 (illustrated in FIGS. 3-4) to be used for either respiration or CPAP and allows for spontaneous breathing along with the traditional non-rebreathing function.

The valve system 1250 comprises a unidirectional valve 1260 and a two-way valve diaphragm 1270 comprising a duck bill valve 1272, and a diaphragm 1275 connected to the duck bill valve 1272. In the exemplary embodiment illustrated in FIG. 12, the duck bill valve 1272 and the diaphragm 1275 are a flexible unitary structure. It is to be understood that other embodiments in which the duck bill valve 1272 is separate from the diaphragm 1275 are contemplated.

Figure 12A:
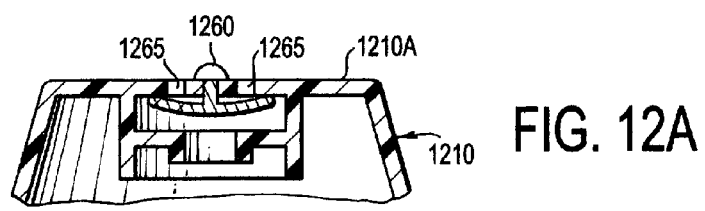
FIG. 12A illustrates an exemplary alternative embodiment of the spontaneous breath valve of FIG. 12, in accordance with an exemplary embodiment of the present invention.

The unidirectional valve 1260 is in a normally closed state in which it seals breath ports 1265 in the housing 1210. Disposed inside of the housing 1210 around the unidirectional valve 1260 is a seal ring 1264, which is configured to provide a seal against the two-way valve diaphragm 1270 during patient exhalation. A view of an alternative embodiment of the unidirectional valve 1260 is illustrated in FIG. 12A.

The rotating outlet port 1220 is rotatably attached to the housing 1210. The outlet port 1220 is configured to rotate relative to the housing 1210 to provide for patient comfort during use. A portion of the rotation outlet port 1220 adjacent to the two-way valve diaphragm 1270 is a seal rim 1224 which is configured to seal against the two-way valve diaphragm 1270 during patient inhalation.

Disposed in the housing adjacent the rotating outlet port 1220 are exhaust ports 1226 and an exhaust seal 1228 for allowing one-way operation of the exhaust ports 1226. In an exemplary embodiment, the exhaust ports 1226 and the exhaust seal 1228 are disposed in the second portion 1210B of the housing 1210.

Operation of the mask connection 1200 is now described. In the mask connection 1200, when air flows into the inlet 1211 in the resuscitation or CPAP mode, it flows through the two-way inlet valve diaphragm 1270, via the duck bill valve 1272, which opens under positive inhalation air flow, to the outlet 1222. This air also forces the diaphragm 1275 of this valve diaphragm 1270 against the seal rim 1224.

Air flows to the mask 130 during gas delivery or when the patient inhales. During patient exhalation, the Duck bill portion 1272 of the two-way valve diaphragm 1270 closes and the exhaled air forces the diaphragm portion 1275 off the seal 1224 and against the seal rim 1264. The outlet 1222 is thereby sealed from the interior space 1211 of the housing 1210. So sealed, the outlet 1222 directs the patient's exhaled air in from the outlet 1222 around the seal rim 1224 and through the exhaust ports 1226 and past the exhaust seal 1228. The exhaust seal 1228 is a one-way exhaust seal that serves as a backup for the diaphragm seal ring 1224 during inhalation to ensure that no air can reverse flow into the exhaust ports 1228.

The unidirectional valve 1260 allows for the patient to breathe spontaneously. Should the patient spontaneously breathe or inhale a volume that is higher than that being delivered at the inlet 1211 of the mask connection 1200, the spontaneous breath valve 1260 opens and allows additional air to flow to the patient through the spontaneous breath ports 1265. This valve 1260 only stay opens if the volume demanded at the output 1222 is higher than the volume at the inlet 1211, i.e., a negative pressure at the inlet 1212 is developed. As soon as the volume demanded at the output 1222 drops below the volume provided at the inlet 1212, the valve 1260 closes and seals the spontaneous breath ports 1265. Thus, the spontaneous breath valve 1265 remains closed during all gas inlet 1212 function unless the patient creates an excess demand. Because the valve system 1250 is proximal to the patient, minimal restriction to airflow is created. This restriction is designed to be no more than 5 cmH$_2$O in negative pressure. Thus, a single valve assembly 1250 breathing circuit can be used for both direct resuscitation and for CPAP wherein spontaneous breathing could occur.

Figure 12B:
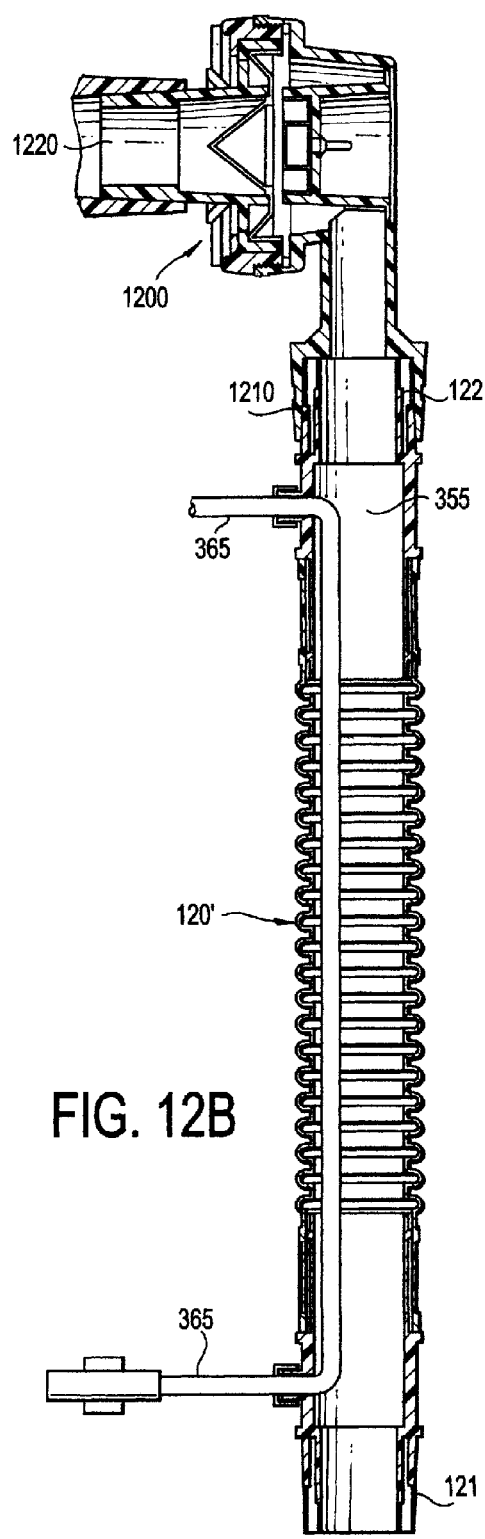
FIGS. 12B and 12C respectively illustrate side cross-sectional and top views of the exemplary embodiment of the mask connection of FIG. 12 connected to the exemplary alternative embodiment of the disposable breathing circuit of FIG. 8C, in accordance with an exemplary embodiment of the present invention.
Figure 12C:
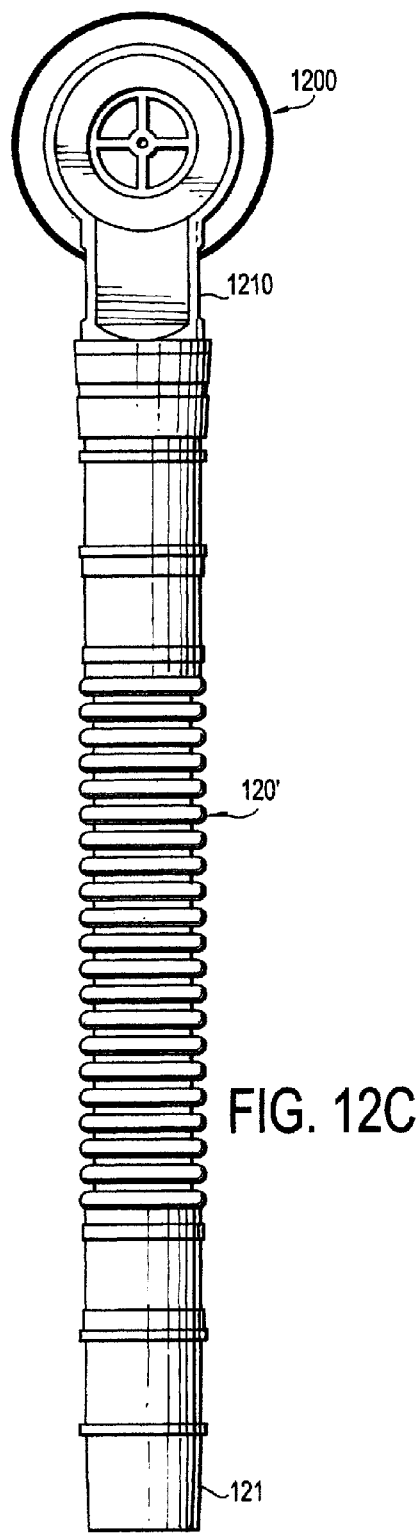

Illustrated in FIG. 12B are exemplary side and top views of the mask connection 1200 attached the second end 122 of the disposable breathing circuit 120', in accordance with an exemplary embodiment of the present invention. The pilot control line 365 is shown unconnected at the first and second ends 121 and 122. It is to be understood that the pilot control line 365 at the first end 121 of the disposable breathing circuit 120' may be connected to the pilot control port 116 of the system 100, and the second end 122 of the disposable breathing circuit 120' may be connected to a pilot connection point on a mask or mask connection, as described herein. FIG. 12B illustrates a closer cross-sectional view of the first end 121 of the disposable breathing circuit 120'.

Figure 13:
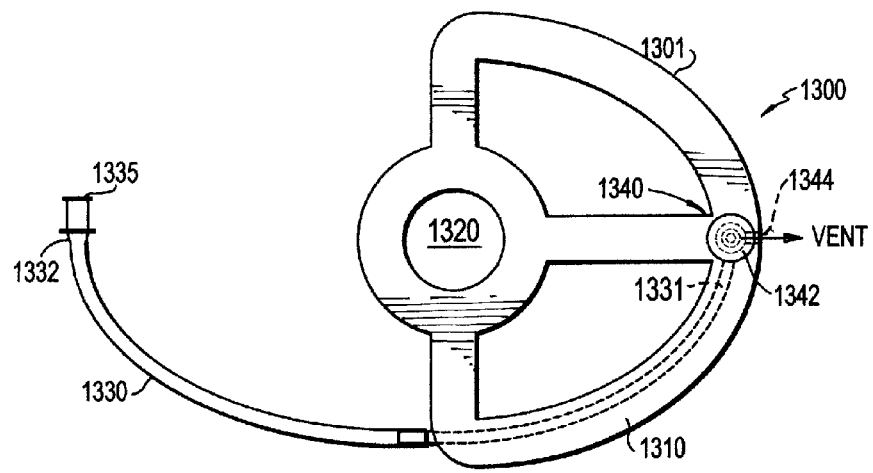
FIG. 13 illustrates an exemplary embodiment of a hand piece for controlling operation of a gas sparing circuit, the hand piece comprising a pilot control switch, in accordance with an exemplary embodiment of the present invention.

Referring now to FIG. 13, there is illustrated a hand piece, generally designated as 1300, in accordance with an exemplary embodiment of the present invention. The hand piece 1300 may be used in cooperation with a conventional mask or the mask of FIG. 17 described below.

The hand piece 1300 comprises a flexible frame 1310 which is configured to fit over a conventional resuscitation mask. The hand piece includes a hole 1320 through which the connection port of the conventional mask passes. Positioned at a first end 1301 of the hand piece 1300 is a pilot control switch 1340 coupled to a vent 1344 for venting a pilot circuit, such as the pilot circuit 360. The switch 1340 and vent 1344 function similarly to the switch 125 and vent 315 illustrated in FIGS. 8A and 8B. A flexible elastomeric switch cap 1342 is placed over the switch 1340 for operating the switch 1340.

The switch 1340 is coupled to a pilot control line extension tube 1330 at a first end 1331 of the tube 1330. Coupled to a second end 1332 of the tube 1330 is a connector 1335 for connecting the tube 1330 to other portions of the pilot control circuit 360.

Figure 14:
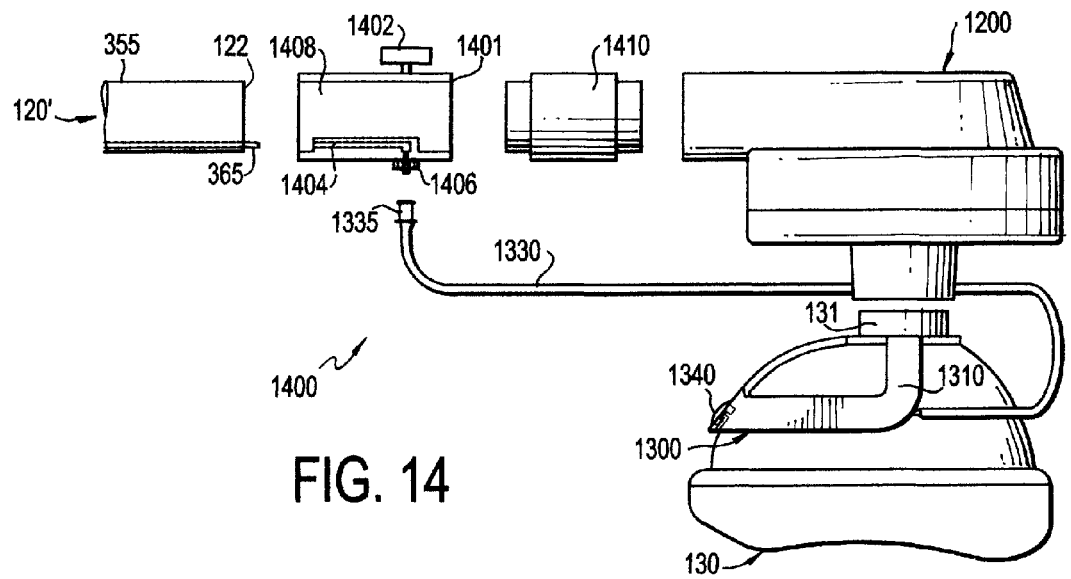
FIG. 14 illustrates an exemplary embodiment of a system incorporating the hand piece of FIG. 13, in accordance with an exemplary embodiment of the present invention.

A system 1400 in which the hand piece 1300 may be used is illustrated in FIG. 14, in accordance with an exemplary embodiment of the present invention. The system 1400 comprises the disposable breathing circuit 120', an adapter 1401 connected to the end 122 of the disposable breathing circuit 120', an optional capnometer 1410 coupled to the adapter 1401, and mask connection 1200 coupled to the capnometer 1410. The mask 130 is connected to the mask connection 1200 via the connection port 131.

The adapter 1401 comprises a positive end-expiratory pressure (PEEP) control 1402 for regulating PEEP through the adapter 1401. The adapter 1401 further comprises a pilot control line 1404 that outputs via an output connection 1406 connected to the luer 1335 and a main gas line 1408 that is connected to the main gas line 355 of the disposable breathing circuit 120'.

As illustrated in FIG. 14, the hand piece 1300 is configured to fit over the mask 130. The hole 1320 of the hand piece 1300 is sized to accommodate the connection port 131 of the mask 130. Activation of air flow through the mask 130 is achieved by depressing the elastomeric switch cap 1342 which actuates the switch 1340 to occlude the pilot control circuit 360, which in the embodiment illustrated in FIG. 14 includes the pilot control line 365, the pilot control line 1404 and the pilot control line extension tube 1330. The gas sparing valve 330 is thereby opened.

Figure 13A:
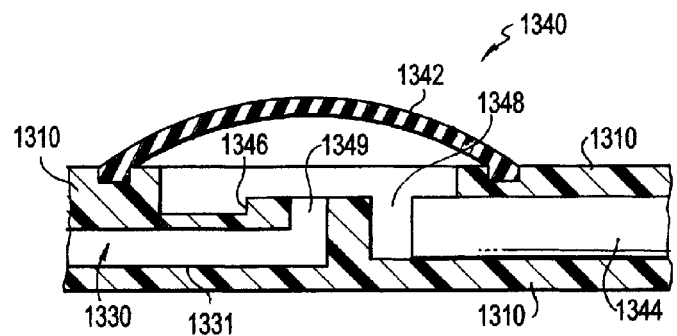
FIG. 13A illustrates an exemplary embodiment of the pilot control switch of FIG. 13, in accordance with an exemplary embodiment of the present invention.

An enlarged view of the pilot control switch 1340 is shown in FIG. 13A, in accordance with an exemplary embodiment of the present invention. The switch 1340 is constructed similarly to the switch 125 illustrated in FIGS. 8A and 8B and operates similarly.

As seen in FIG. 13A, the switch 1340 is formed by the elastomeric membrane 1342 which is attached to the frame 1310 of the hand piece 1300 over a chamber 1348. The end 1331 of pilot control line 1330 is disposed within the frame 1310 and opens to the chamber 1348 at an opening 1349. A seal ridge 1346 is disposed around the opening 1349 of the pilot control line 1330.

When the elastomeric membrane 1342 is in the state shown in FIG. 13A, i.e., when it is in a non-depressed state, pilot gas passes through the pilot control line 1330, out the opening 1349, through the air chamber 1348, and out the vent port 1344. Under this condition, the gas sparing valve 330 is not activated and there is no flow in the primary gas circuit 305. When the elastomeric switch element 1342 is depressed against the seal ridge 1346, the pilot gas air flows out the vent 1344 is occluded, thereby activating the gas sparing valve 330 and allowing primary gas to flow through the primary gas circuit 350 until the elastomeric switch element 1342 is released.

Figure 15:
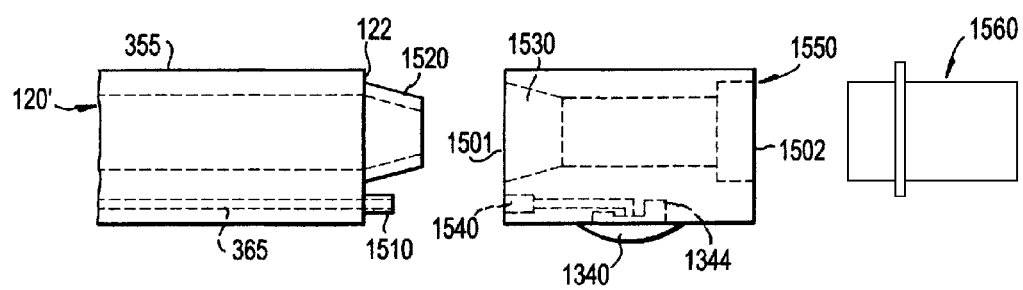
FIG. 15 illustrates an exemplary embodiment of an endotracheal hand piece for control operation of a gas sparing circuit, in accordance with an exemplary embodiment of the present invention.

In addition to the hand piece 1300 described above, a simple hand piece that could be used without a mask, and used with other resuscitation apparatus such as an endotracheal tube, is contemplated. Illustrated in FIG. 15 is an endotracheal tube hand piece (also referred to herein as "endotracheal tube adapter") 1500, in accordance with an exemplary embodiment of the present invention. The endotracheal hand piece 1500 is configured to be used with the disposable breathing circuit 120'. The disposable breathing circuit 120' differs from the disposable breathing circuit 120 in that the disposable breathing circuit 120' does not include the pilot control switch 125 or the vent 351. Instead, the pilot control line 365 extends through the entire length of the disposable breathing circuit 120' to the second end 122. The end 122 of the disposable breathing circuit 120' comprises an outlet 1510 of the pilot control line 365 and an outlet 1520 of the main gas line 355.

The endotracheal hand piece 1500 comprises a first end 1501 comprising an inlet port 1530 and an inlet port 1540. The port 1540 is configured to receive the outlet port 1510 of the pilot control line 365. The port 1540 is coupled to the pilot control switch 1340 and the vent 1344. The port 1530 is configured to receive the outlet port 1520 of the main gas line 355. The port 1530 communicates with an endotracheal tube connection 1550 at a second end 1502 of the endotracheal hand piece 1500. The switch 1340 is operated as described above to control the main gas line 355. When operated, the switch 1340 actuates the gas sparing valve 330 to provide primary gas through the main gas line 355, to the port 1530, and to an endotracheal tube 1560 connected to the connection 1550.

Figure 16A:
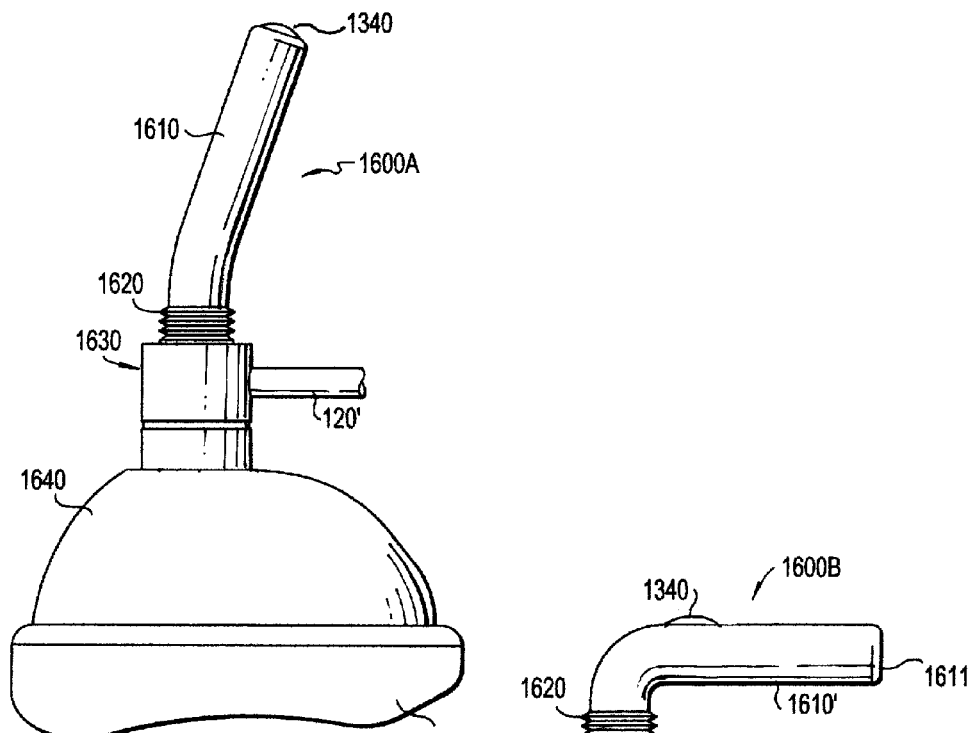
FIGS. 16A and 16B illustrate exemplary alternative embodiments of masks with integrated hand pieces for control operation of a gas sparing circuit, in accordance with an exemplary embodiment of the present invention.
Figure 16B:
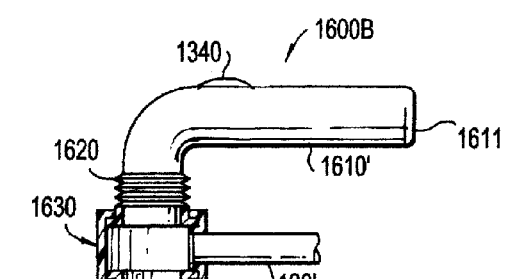

Alternative exemplary embodiments of the hand piece 1300 are illustrated in FIGS. 16A and 16B, in accordance with an exemplary embodiment of the present invention. Illustrated in FIG. 16A is a hand piece 1600A, which is, generally, a combination of the hand piece 1300 and the mask connection 1200, in accordance with an exemplary embodiment of the present invention. The hand piece 1600A comprises a handle 1610, a body portion 1630, and a mask 1640. The mask 1640 may be rotatably connected to the body portion 1630. The body portion 1630 is connected to the handle 1610 by a pliant section 1620, which allows for the handle 1610 to bend relative to the body portion 1630.

The disposable breathing circuit 120' is connected to the hand piece 1600A via a rotatable coupling 1640. The rotatable coupling 1640 allows for the position of the disposable breathing circuit 120' to be positioned for patient comfort when the mask is installed on the patient. Activation of the gas sparing system is by way of the elastomeric element 1340. It is to be understood that the hand piece 1600A may be used in any of the systems for delivering gas to a patient and gas sparing circuits described herein.

Illustrated in FIG. 16B is a hand piece 1600B, which is also, generally, a combination of the hand piece 1300 and the mask connection 1200, in accordance with an exemplary embodiment of the present invention. The hand piece 1600B comprises all of the elements of the hand piece 1600A, with a few modifications. The hand piece 1600B comprises an L-shaped handle 1610' rather than the mostly vertical handle 1610 of the hand piece 1600A. In one embodiment, the disposable breathing circuit 120' may be connected to the rotating body portion 1630 of the hand piece 1600B. In another embodiment, an end 1611 of the handle 1610' is configured to receive the end 122 of the disposable breathing circuit 120'.

Figure 17:
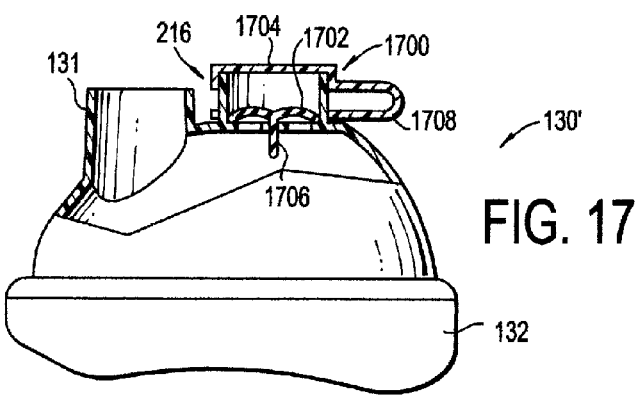
FIG. 17 illustrates an exemplary embodiment of a mask with a CPAP port for use with a system providing resuscitation and CPAP air delivery, in accordance with an exemplary embodiment of the present invention.

Referring now to FIG. 17, there is illustrated an exemplary embodiment of the patient mask 130', in accordance with an exemplary embodiment of the present invention. The patient mask 130' is used with a gas sparing circuit, such as the gas sparing circuit 400 of the gas delivery system 400, in which both resuscitation and CPAP gas delivery modes are desired. The mask 130' comprises the CPAP port 216 described above with respect to FIG. 2. FIG. 17 illustrates the CPAP port 216 in further detail.

The CPAP port 216 comprises a vent port 1700 comprising valve housing 1702 integrated with the mask 130'. The valve housing 1702 is capped by a removable cap 1704, which is tethered to the housing 1702 by a lanyard 1708. Disposed within the valve housing 1702 is a one-way valve 1706. When the mask 130' is used with the system 200, and the system 200 is operating in resuscitation mode, the cap 1704 is placed over the port 1700 to not allow resuscitation gas to bypass the patient and exit the mask 130'. When operating in CPAP mode, the cap 1704 is removed to allow exhalation breath.

In the case that the mask 130' is used with the mask connection 1200, exhalation through the ports 1226 is not possible as the diaphragm 1275 is in the open position in the CPAP mode. Thus, a second exhalation port is provided via the exhalation port in the mask in FIG. 17. Thus, the vent port 1700 allows for an exhalation breath along with inlet gas flow exhaust for pressure relief within the mask 130' during CPAP mode so that the pressure within the mask 130' during use is maintained at a controlled level.

Figure 18:
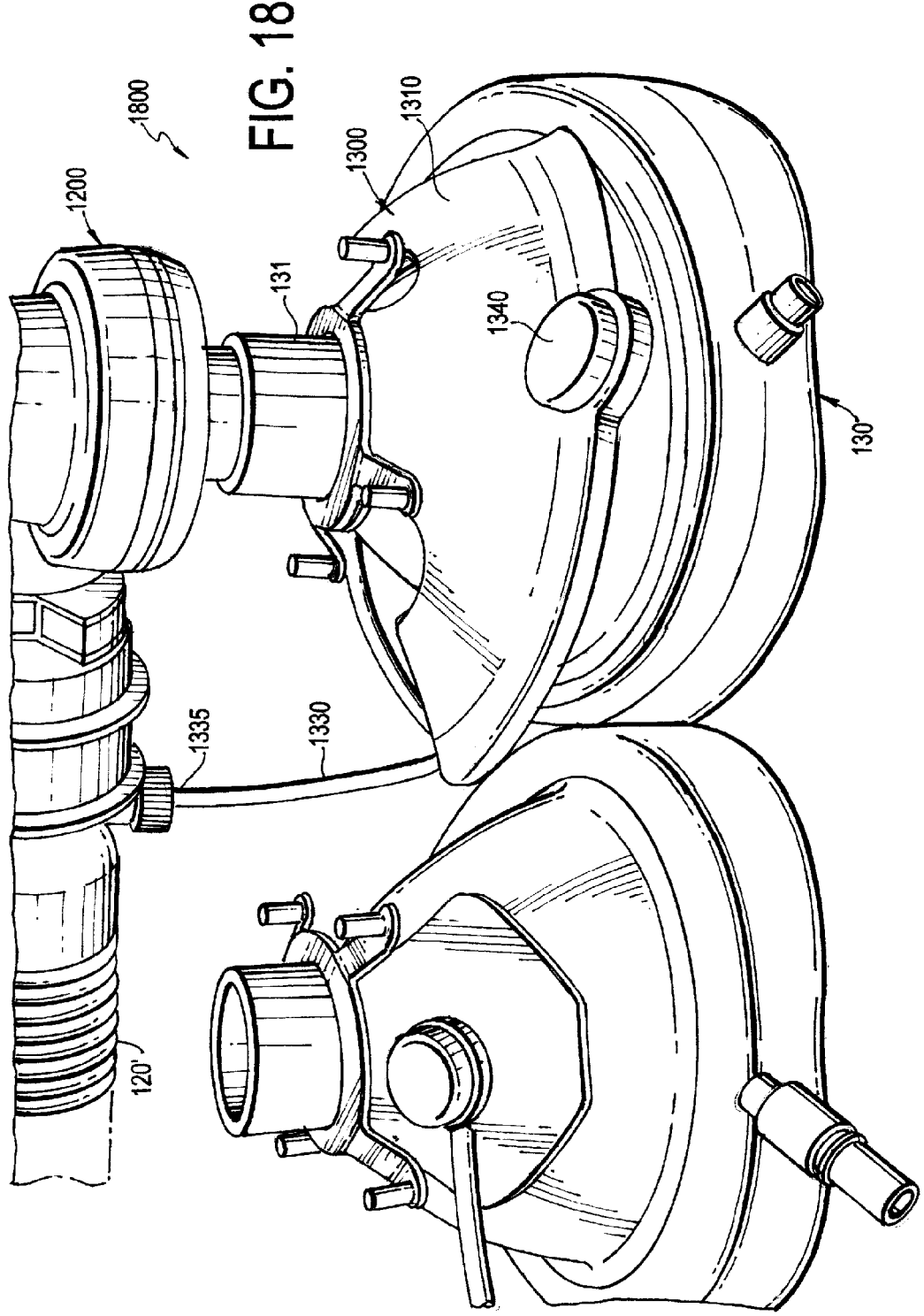
FIG. 18 illustrates another view of the exemplary embodiment of the hand piece of FIG. 13 showing the pilot control switch attached to the mask, in accordance with an exemplary embodiment of the present invention.

FIG. 18 illustrates another embodiment of a system, generally designated as 1800, comprising the disposable breathing circuit 120', the mask connection 1200, the mask 130, and the hand piece 1300, in accordance with an exemplary embodiment of the present invention. The connector 1335 of the hand piece 1300 is connected to the second end 122 of the pilot control line 365 of the disposable breathing circuit 120'. The first end 1212 of the mask connection 1200 is connected to the second end 122 of the main gas line 355 of the disposable breathing circuit 120', and the second end 1222 of the mask connection 1200 is connected to the connection port 131 of the patient mask 130. Activation of air flow through the mask 130 is achieved by depressing the elastomeric switch cap 1342 (Should this be 1340) which actuates the switch 1340 to occlude the pilot control circuit 360, which in the embodiment illustrated in FIG. 18 includes the pilot control line 365 and the pilot control line extension tube 1330. The gas sparing valve 330 is thereby opened. Although FIG. 18 illustrates using the mask 130 in the system 1800, it is to be understood that the mask 130' may be also used.

Figure 19:
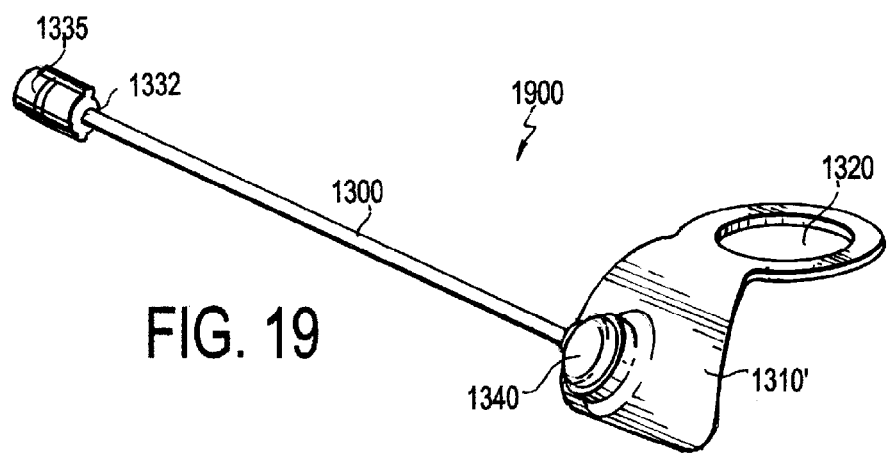
FIG. 19 illustrates an exemplary alternative embodiment of a hand piece for controlling operation of a gas sparing circuit, in accordance with an exemplary embodiment of the present invention.

FIG. 19 illustrates an exemplary alternative embodiment of the hand piece of FIG. 13, generally designated as 1900 in FIG. 19, in accordance with an exemplary embodiment of the present invention. The hand piece 1900 includes all of the components of the hand piece 1300, but the frame 1310 is modified as a frame 1310' having a smaller profile.

Figure 20A:
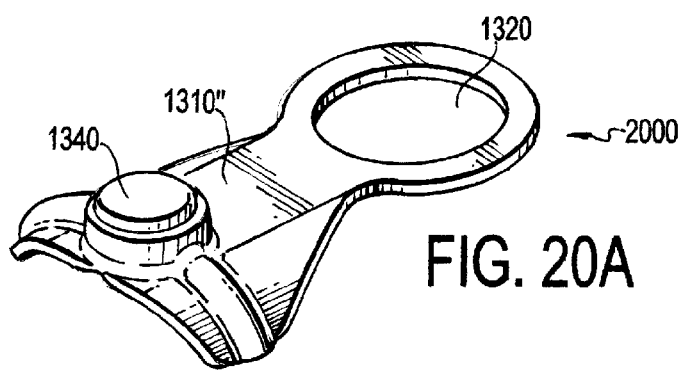
FIGS. 20A through 20C illustrate various views of another alternative embodiment of a hand piece for controlling operation of a gas sparing circuit, in accordance with an exemplary embodiment of the present invention.
Figure 20B:
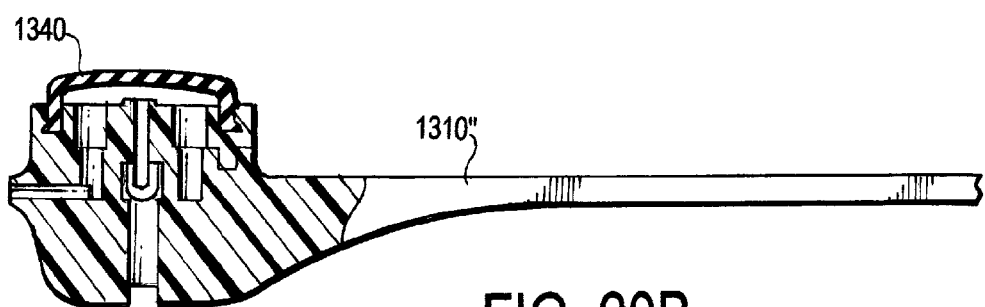
Figure 20C:
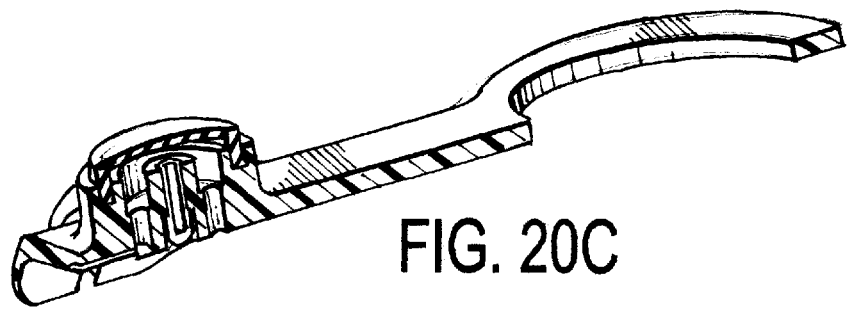
Figure 23C:
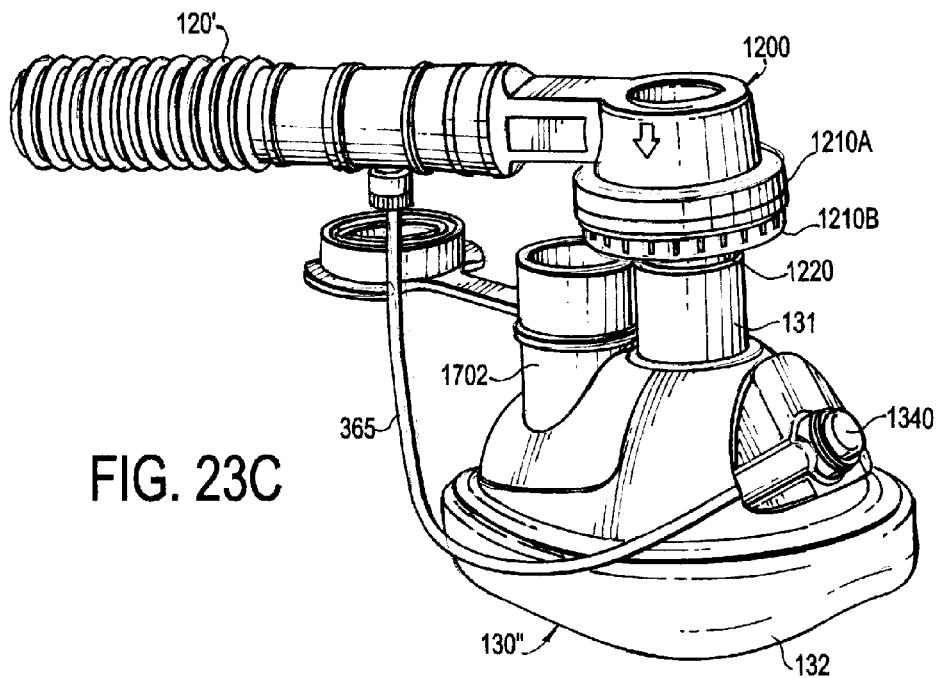
Figure 23D:
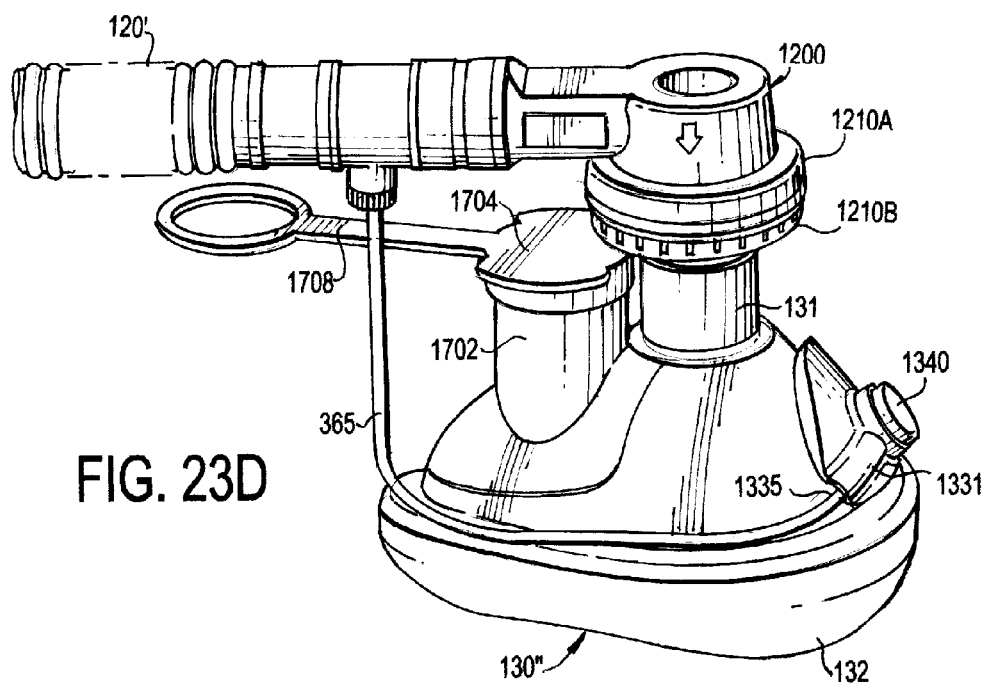

FIGS. 20A-20C illustrate various views of yet another alternative embodiment of the hand piece of FIG. 13, generally designated as 2000 in FIGS. 20A-C, in accordance with an exemplary embodiment of the present invention. The hand piece 2000 includes all of the components of the hand piece 1300, but the frame 1310 is modified as a frame 1310" having a smaller profile.

Figure 22A:
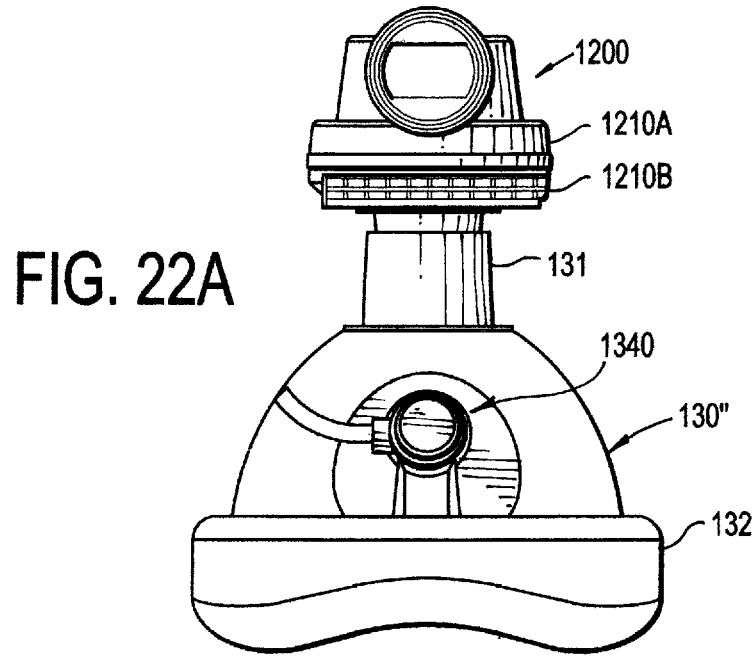
FIGS. 22A through 22C illustrate various views of another exemplary embodiment of a mask with a CPAP port for use with a system providing resuscitation and CPAP air delivery, in accordance with an exemplary embodiment of the present invention.
Figure 22B:
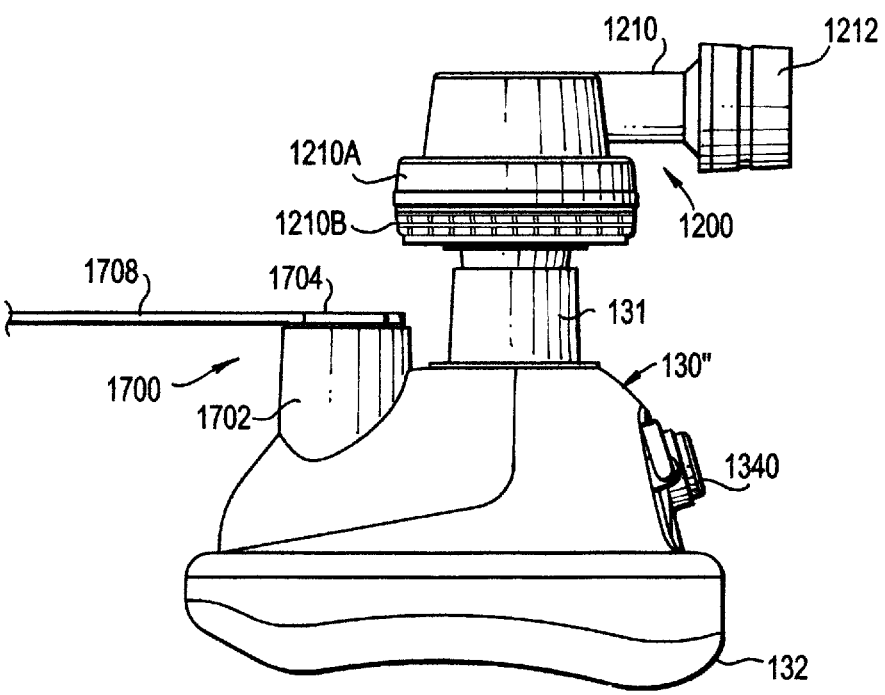
Figure 22C:
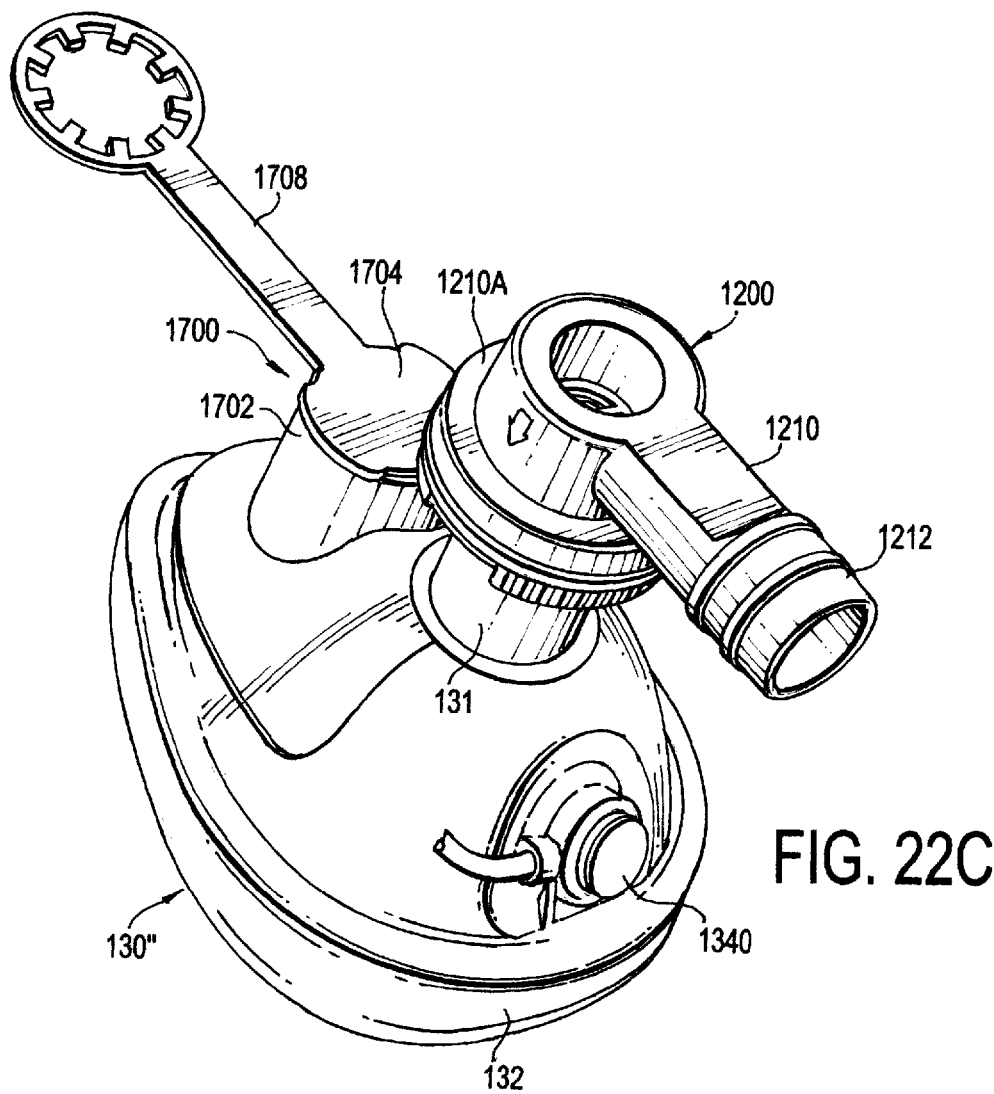

Referring now to FIGS. 22A through 22C, there are illustrated, respectively, front, side, and perspective views of an alternative embodiment of the patient mask 130', generally designated in FIGS. 22A-22C as 130", in accordance with an exemplary embodiment of the present invention. The patient mask 130" is similar to the patient mask 130', particularly in that it includes the CPAP vent port 1700. The patient mask 130" differs, however, in that it further includes the pilot control switch 1340, which is disposed on the patient mask 130" in the embodiment illustrated, rather than on a hand piece. FIGS. 23A through 23F illustrate various views of various components of a combination of the patient mask 130" connected to the mask connection 1200, which is connected to the disposable breathing circuit 120', in accordance with an exemplary embodiment of the present invention.

Figure 24:
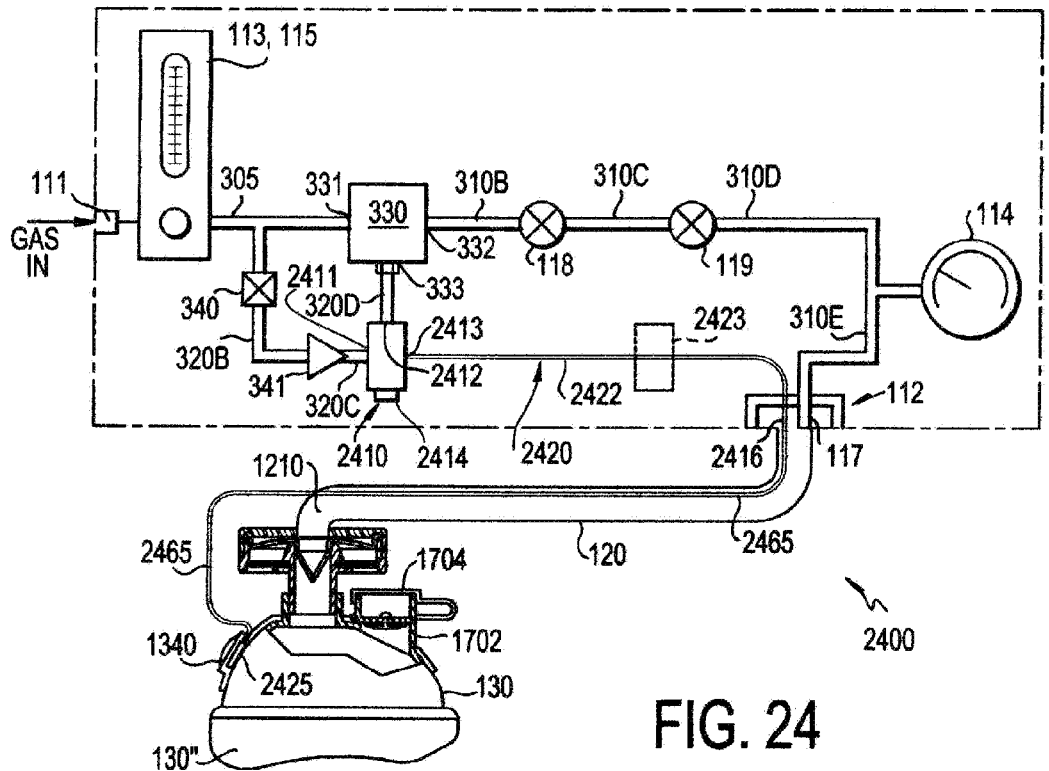
FIG. 24 illustrates an exemplary block diagram of an exemplary embodiment of a system for delivering gas to a patient using electrical solenoid and electrical switch control of a pilot control branch, in accordance with an exemplary embodiment of the present invention.

Referring now to FIG. 24, there is illustrated an exemplary alternative embodiment of the gas sparing circuit 300, generally designated in FIG. 24 as 2400, in accordance with an exemplary embodiment of the present invention. In this gas sparing circuit 2400, the manual pneumatic pilot control line 365 of the breathing circuit 120 or 120' is replaced by an electrical switch-activated pilot control line 2465, and the mechanical pilot control switch 125 is replaced by an electric switch 2425, as shown in FIG. 24. The electrical switch 2425 is placed under a pliant cap 1340 on the mask 130". The gas sparing circuit 2400 uses all the components illustrated in FIG. 3, modified as described below, and additional components as illustrated in FIG. 24. For example, the gas sparing circuit 2400 incorporates the main gas branch 310 and the pilot control branch 320, as modified to include an electrical pilot control branch 2420 and an electrical pilot control line 2465. In another exemplary embodiment, a CPAP branch, such as the CPAP branch 430 of FIG. 4, could also be added to the gas sparing circuit 2400 to add CPAP functionality.

The electrical pilot control branch 2420 of the gas sparing circuit 2400 is an electronic control circuit which comprises an electric solenoid valve 2410 configured to control the gas flow to the main gas sparing valve 330. The electrically controlled solenoid 2410 is a normally open valve that allows pilot gas to vent to the atmosphere through a vent port 2414. The pilot input 320C is coupled to the valve 2410 at an inlet 2411. The outlet 2412 of the valve 2410 is coupled to the portion 320D of the pilot control branch 320.

The valve 2410 operation is controlled electrically through the pilot control circuit 360, specifically the electrical pilot control branch 2420, the electrical pilot control line 2465, and the switch 2425. The electrical pilot control branch 2420 comprises wires 2422 and an optional timer circuit 2423, and the electrical pilot control line 2465 is formed from wires. The optional timer circuit 2423 functions to control the on time and off time of the valve 2410 and, therefore, the on and off time of the gas sparing valve 330, thereby providing for continued cycling of the gas sparing valve 330 when activated. The pilot control line 2465 replaces the pilot control line 365 of FIG. 3. The pilot control line 2465 couples to the connector 112 at a connection (input) 2416, thereby creating a complete electrical circuit with the electrical pilot control branch 2420.

Operation of the gas sparing circuit 2400, with electronic solenoid control, is now described. Operation begins with the solenoid valve 2410 in the normally closed state which allows pilot branch 1420 to be in the occluded state. In this condition the pilot gas does not flow past the solenoid valve 2410 into the pilot control line 320D. The gas sparing valve 330 remains closed as the pilot line 320D on the gas sparing valve control side is vented to atmosphere, $P_{atm}$. Upon closure of electrical switch 2425, by depression of the pliant switch cap 1340 on the mask 130", an electrical signal is sent through the wires 2465 and 2422, and the solenoid valve 2410 is activated. Pilot gas flow is directed into pilot line 320D. Pilot gas at pressure $P_B$ is applied to the control side 333 of the gas sparing valve 330, and the valve 330 opens allowing gas to flow into the main gas side 310, as described above with respect to FIGS. 3, 6, and 7. The solenoid valve 2410 remains activated, and main gas continues to flow until the switch 2425 is released and the signal to the solenoid valve 2410 is deactivated. Upon deactivation of the solenoid valve 2410, the pilot gas in the circuit 2460 is occluded, and pilot gas in the line 320D is vented to atmosphere through the vent port 2414. Pressure in the control side 333 of the gas sparing valve 330 drops to $P_{atm}$, and the gas sparing valve 330 closes, thereby stopping main gas flow through the circuit 310. This operation can is repeated manually for each desired breath by depressing the pliant mask switch cap 1340.

In an alternative exemplary embodiment of the gas sparing circuit 2400, there is an optional timer circuit 2423 that will allow for cycling of the electrically controlled solenoid valve 2410 for the auto breath function with settable on and off times for resuscitation. In this configuration and any of the timer configurations described herein, the mask switch 2425 could have a hold-closed latch to allow for the auto breath function to continue after latching the switch closed so the user does not have to hold the switch in place.

It is to be understood that the gas sparing circuit 2400 may be modified as described herein to provide for CPAP functionality as shown in FIG. 4 and/or to include an internal gas supply.

Figure 25:
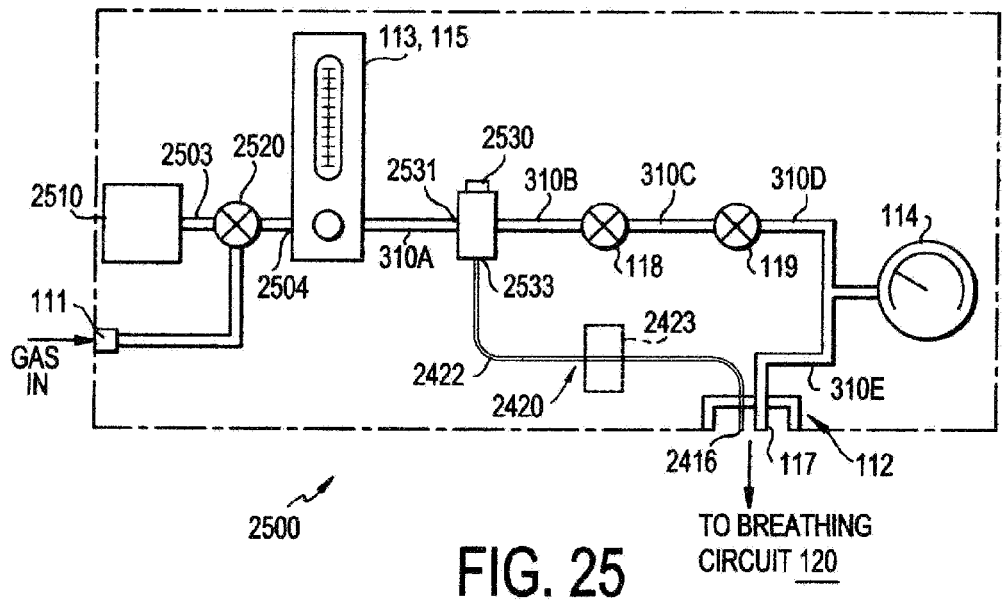
FIG. 25 illustrates an exemplary block diagram of an exemplary embodiment of a system for delivering gas to a patient using electrical switch control of a gas sparing valve, in accordance with an exemplary embodiment of the present invention.

FIG. 25 illustrates a block diagram for yet another exemplary embodiment of a gas sparing circuit, generally designated as 2500, in accordance with an exemplary embodiment of the present invention. The gas sparing valve 2530 in this embodiment is an electrically activated solenoid valve 2530 which is controlled through a mask switch, such as the mask switch 2425. In this embodiment, in addition to the external gas inlet 111, there may be an internal air generation-supply module 2510, which can create the desired gas pressure and flow on demand to an outlet 2503. A selector valve 2520 is used to select the appropriate gas source from the inlet 111 or the internal air generation-supply module 2510.

Operation of the electrically controlled main gas solenoid valve 2530 is controlled electrically through the electrical pilot control circuit 2460. The solenoid valve 2530 is connected through the wires 2422 of the electrical pilot control branch 2420 to an external electrical pilot control line, e.g., the electrical pilot control line 2465, and to a switch, e.g., the switch 2425. In an exemplary alternative embodiment, the electrical pilot control branch include the optional timer circuit 2423 that functions to control the on time and off time of the valve 2530 and, therefore, the on and off time of the main gas flow to the patient.

Operation of the gas circuit 2500, with electronic solenoid control, is now described. Operation begins with the solenoid valve 2530 in the normally closed state which does not allow main gas flow through the main gas circuit 350. Upon closure of the electrical switch 2425 by depression of the pliant switch cap 1340 in the mask 130", an electrical signal is sent through the wires 2465 and 2422, and the solenoid valve 2530 is activated. Main gas flow is directed through the main gas branch 310. The solenoid valve 2530 remains activated and main gas continues to flow until the switch 2425 is released, at which time the signal to the solenoid valve 2530 is deactivated. Upon deactivation of the solenoid valve 2530, main gas flow stops. This operation can is repeated manually for each desired breath by depressing the pliant mask switch cap 1340.

In addition there is an optional timer circuit 2423 that will allow for cycling of the electrically controlled solenoid valve 2530 for the auto breath function with settable on and off times for resuscitation. In this configuration and any of the timer configurations described herein, the mask switch 2425 could have a hold closed latch to allow for the auto breath function to continue after latching the switch closed so the user does not have to hold the switch in place.

It is to be understood that the gas sparing circuit 2500 may be modified as described herein to provide for CPAP functionality as shown in FIG. 4 and/or to include an internal gas supply 2510, i.e., the internal supply 2510 is optional. Also, it is contemplated that the gas sparing circuit 2500 can be applied directly to either the internal gas supply 2510 or an external gas supply via the inlet 111 to provide a time controlled breath pulse through the outlet 2503 to the main gas side 310 and thus to the patient through the port 117.

Figure 26B:
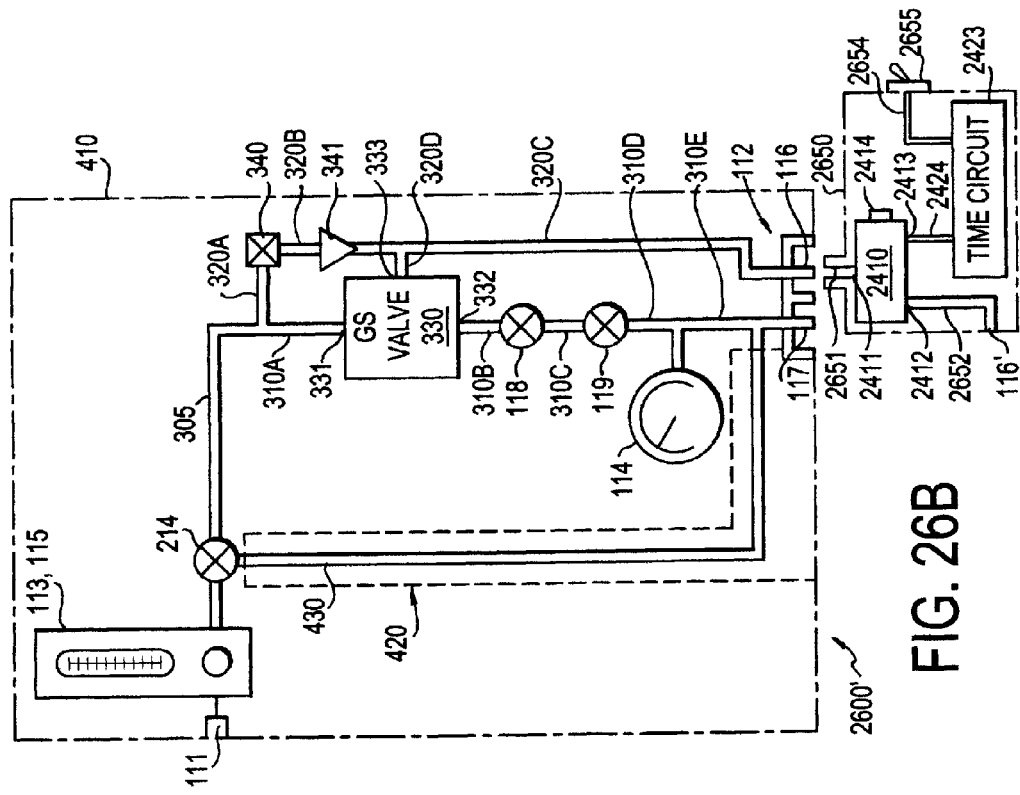
FIG. 26B illustrates an exemplary block diagram of an exemplary embodiment of a gas sparing circuit of using selectable manual pilot line control of a gas sparing valve and electrical timer control of the gas sparing valve contained in an external, removable module, in accordance with an exemplary embodiment of the present invention.
Figure 26A:
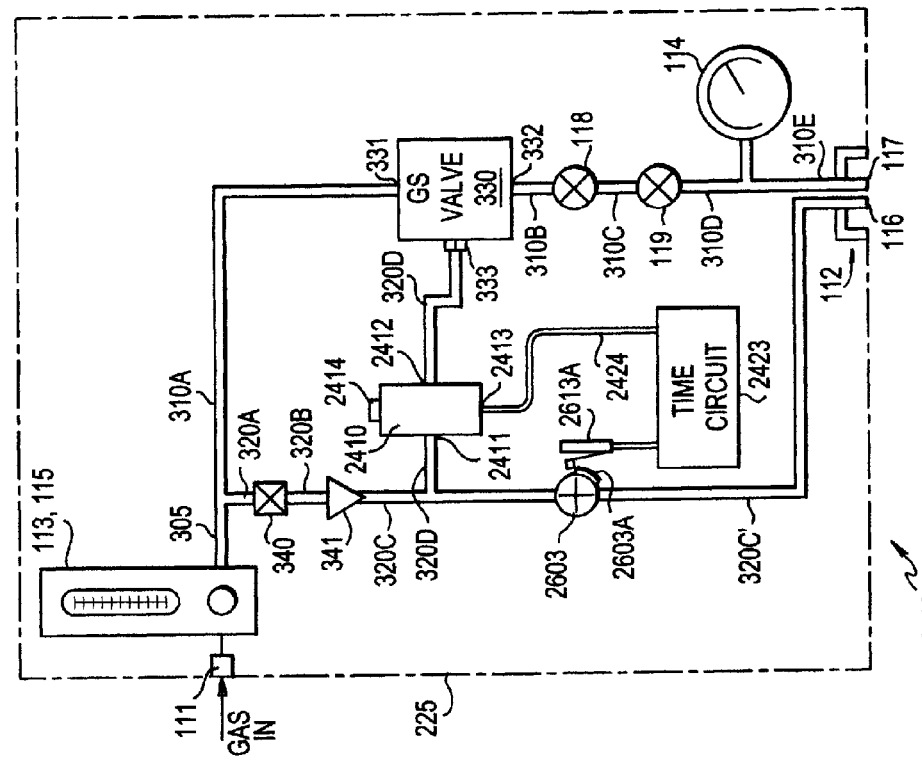
FIG. 26A illustrates an exemplary block diagram of an exemplary embodiment of a gas sparing using selectable manual pilot line control and electrical timer control of a gas sparing valve, in accordance with an exemplary embodiment of the present invention.

FIG. 26A illustrates and describes a block diagram for still another exemplary embodiment of a gas sparing circuit, generally designated as 2600, in accordance with an exemplary embodiment of the present invention. This gas sparing circuit 2600 includes both pneumatic manual pilot control functionality and automatic electronic-based auto breath control that is activated by way of a pneumatic valve/switch actuator 2603 disposed in the gas line portion 320C. The pneumatic valve/switch actuator 2603 includes a toggle 2603A for toggling between manual and automatic positions. When the pneumatic valve/switch actuator 2603 is switched to the automatic position, the gas sparing circuit 2600 cycles electro-pneumatically in an automatic manner until the switch 2603 is set back to the manual position or gas pressure is removed from the pilot line. This gas sparing circuit 2600 includes both the manual pilot control functionality of FIG. 3 (the manual pneumatic pilot control line 365 and the mechanical pilot air flow control switch 125) and the electrical switch-activated pilot control of FIG. 24 (the solenoid valve 2410 and electrical pilot control branch 2420 with the electronic timer circuit 2423) for auto breath capability. The solenoid valve 2410 is disposed in the portion 320D connected to the control side 333 of the gas sparing valve 330.

Operation of the gas circuit 2600, with manual pilot control and electrical switch-activated pilot control for auto breath capability, is now described. Operation of the gas sparing circuit 2600 is identical in operation to FIG. 3 when the pneumatic valve/switch actuator 2603 is in the manual gas control position for utilization of the pilot control circuit 320, specifically the pilot control line 365 and flow control switch 125. In this configuration the electronically controlled solenoid valve 2410 is in a normally open configuration when no control signal is provided and pilot gas can pass through the solenoid valve 2410 freely.

When the pneumatic valve/switch actuator 2603A is set in the manual position, pilot gas flows through the pilot control line 320C. When the pilot control line 365 is occluded by use of the flow control switch 125, the pilot circuit 320C becomes occluded, thereby allowing pilot gas to flow through the solenoid valve 2410 and the control line 320D. Pilot gas at pressure $P_B$ is applied to the control side 333 of the gas sparing valve 330, and the valve 330 opens, thereby allowing gas to flow into the main gas branch 310, as described above with respect to FIGS. 3, 6, and 7. Releasing the mask switch 125 causes the pressure to drop in the pilot line 320D and at control side 333 of the gas sparing valve 330, and the valve 330 closes, thereby stopping gas flow into the main gas branch 310, as described above with respect to FIGS. 3, 6, and 7.

When the pneumatic valve/switch actuator 2603 is set in the auto breath position, a toggle 2613A electrically connected to the electronic timer circuit 2423 is closed, and the electronic time circuit 2423 is energized. Additionally, gas is directed to the pilot line 320D and the control side 333 of the gas sparing valve 330, which opens to allow gas flow through the main gas side 310. At this time, the electronic timer circuit 2423 begins to cycle the electronic solenoid valve 2410 between the normally open position, which allows pilot gas flow through its outlet 2412 to the gas sparing valve 330, and the closed position, in which the solenoid 2410 stops pilot flow to the outlet 2412 and to the gas sparing valve 300 at the control side 333. In the closed position of the electronic solenoid 2410, flow is closed at inlet 2411, but flow is then opened at the vent 2414, which allows the pilot control line 320D to vent and the pressure at the control side 333 to drop to $P_{atm}$, thereby closing the gas sparing valve 330 and stopping flow in the main gas side 310. The electronic timer 2423 cycles the solenoid valve 2410 between the closed and open state creating a controlled auto breath function that can be user adjusted for on time and off time. This operation continues until the valve/switch actuator 2603 is set back to the manual position by way of the toggle 2603A.

It is to be understood that the gas sparing circuit 2400 may be modified as described herein to provide for CPAP functionality as shown in FIG. 4 and/or to include an internal gas supply, as shown in FIG. 25.

Now turning to FIG. 26B, there is illustrated a block diagram for yet another exemplary embodiment of a gas sparing circuit 2600', in accordance with an exemplary embodiment of the present invention. This gas sparing circuit 2600' includes both the manual pilot control functionality of FIGS. 3 and 4 (the gas sparing circuit 400) and the electrical switch-activated pilot control of FIG. 24 (the electrically controlled solenoid pilot valve 2410) for auto breath capability with the exception that the electrical switch-activated pilot control valve 2410 is located in a removable accessory enclosure 2650 external to the gas sparing circuit 400 and is attached to the pilot control port 116 at outlet 112. An electrical switch 2655 in the accessory enclosure 2650 activates the electronic pilot circuit control.

The gas sparing circuit 2600' incorporates a gas sparing configuration identical to the gas sparing circuit 400 shown in FIG. 4 and includes the resuscitation side 410 and the CPAP side 420. In addition to including the gas sparing circuit 400, the gas sparing circuit 2600' further includes the removable auto breath control module 2650 connected to the outlet port 116 of the gas sparing circuit 400. The removable auto breath control module 2650 includes its own pilot control port 116'. When not installed, the breathing circuit 120 or 120' can be attached to the gas port 112 (described above with respect to FIG. 4). When the auto breath control module 2650 is attached to the pilot control port 116, the pilot control line 365 of the breathing circuit 120 or 120' can still be connected to the pilot control port 116' for manual operation.

The auto breath control module 2650 includes an inlet line 2651, which connects to the pilot control port 116, and an outlet line 2652, which connects to a pilot outlet port 116'. An electronic solenoid valve 2410 is connected between the inlet and outlet lines 2651 and 2652. Specifically, an inlet 2411 of the electronic solenoid valve 2410 is connected to the inlet port 2651, and an outlet 2412 of the electronic solenoid valve 2410 is connected to the outlet port 2652. A timer circuit 2433 is connected to the electronic solenoid valve 2410 through wires 2424 and to a control switch 2655 via wires 2654. The pilot control line 365 of circuit 120 connects to outlet port 116' of the auto breath control module and provides for manual control.

Operation of the gas circuit 2600' of FIG. 26B, with manual pilot control and electrical switch-activated pilot control for auto breath capability, is now described. The external auto breath module 2650 is attached to the gas control circuit 410 through the inlet line 2651 of the auto breath control module 2650 which is connected to the pilot port 116 of the main gas circuit 410. The output line 2652 is provided from the auto breath control module 2650 for connection to the pilot control line 365 of breathing circuit 120. For operation of gas circuit 2600', the main gas line 355 of breathing circuit 120 is connected to outlet port 117, as described with respect to FIGS. 3 and 4. The pilot control line 365 of breathing circuit 120 is connected to the outlet port 116' of the auto breath control module 2650.

When the auto breath control module control switch 2655 is in the Off position the electronic solenoid valve 2410 is in the normally open position allowing pilot gas to flow unrestricted through the solenoid valve 2410. Then operation of the gas sparing circuit 2600' is identical in operation to that described in FIGS. 3 and 4 with manual control of the main gas line 320 provided through activation of the pilot control switch 125.

If auto breath functionality is desired, the control switch 2655 on the auto breath control module 2650 is switched to the On position. The timer circuit 2423 is energized and then cycles the solenoid valve 2410 from the normally open position to the normally closed position. The pilot line 320C is then occluded at solenoid input 2651 and pilot gas flow is directed into the pilot control line 320D. Pilot gas at pressure $P_B$ is applied to the control side 333 of the gas sparing valve 330, and the valve 330 opens allowing gas to flow into the main gas side 310, as described above with respect to FIGS. 3, 6, and 7. The solenoid valve 2410 remains activated, and main gas continues to flow until the timer 2423 cycles the solenoid valve 2410 to the normally open position, at which time the solenoid valve 2410 vents the pilot line 320C through the solenoid valve to the pilot control line 365 and out vent port 351 on the mask switch 125. At this time pressure in the control side 333 of the gas sparing valve 330 drops to $P_{atm}$, and the gas sparing valve 330 closes, thereby stopping main gas flow through the circuit 310. The electronic timer 2423 cycles the solenoid valve 2410 between the closed and open state to create a controlled auto breath function that can be user adjusted for on time and off time. This operation continues until the control switch 2655 is set back to the Off position.

It is to be understood that an alternate embodiment for the external electronic auto breath control module 2650 would be to utilize pneumatic timers such as those illustrated in FIG. 10, FIG. 27, and FIGS. 28 and 29, and a pneumatic valve/switch as necessary but in a configuration where the pneumatic timers would be located within an external removable module, as described in FIG. 26B. In another exemplary embodiment, CPAP branch portion 430B could be connected to main branch portion 310B allowing the pressure relief valve 118 to be disposed downstream of the connection with the portion 430B. In such embodiment, the pressure relief valve 118 provides venting for overpressure in either the CPAP branch 430 or the primary branch 310. Furthermore, it is to be understood that the gas sparing circuit 2400' may be modified to include an internal gas supply.

Figure 27:
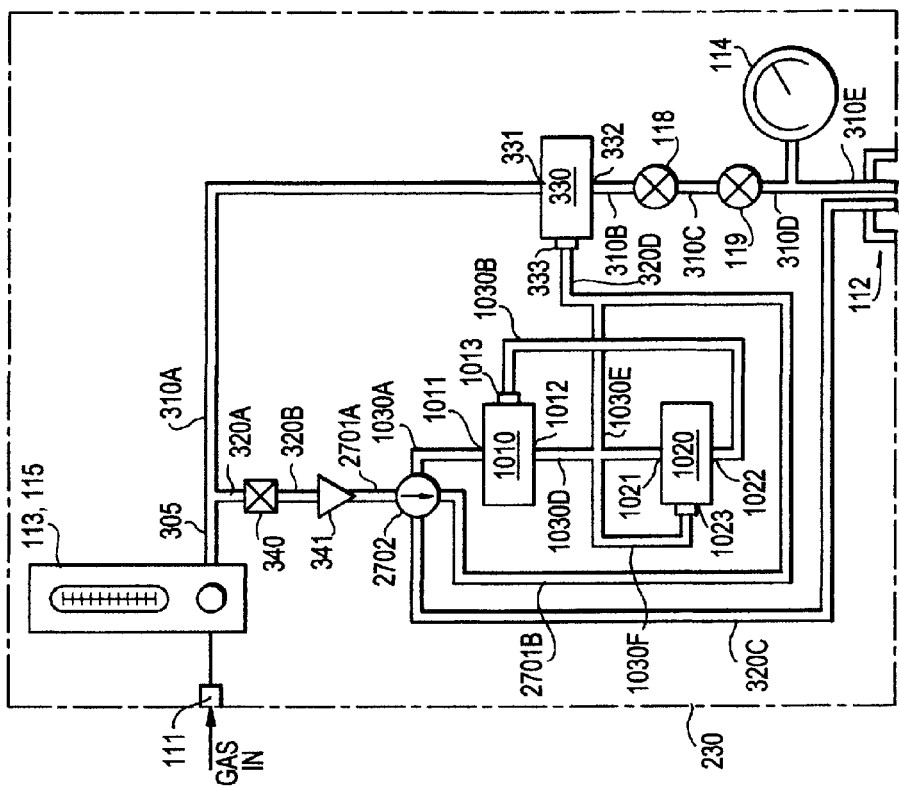
FIG. 27 illustrates an exemplary block diagram of an exemplary embodiment of a gas sparing circuit using selectable manual pilot line control of a gas sparing valve and pneumatic timer control of the gas sparing valve, in accordance with an exemplary embodiment of the present invention.

FIG. 27 illustrates still another exemplary embodiment of a gas sparing circuit, generally designated as 2700, in accordance with an exemplary embodiment of the present invention. This gas sparing circuit 2700 includes both pneumatic manual pilot control functionality through the attached circuit and automatic pneumatic timer based auto breath control set with a switch on the gas control unit instead of having to hold the manual pilot line occluded. Once switched to automatic, the gas sparing circuit 2700 cycles pneumatically until the switch is set back to manual or gas pressure removed from the pilot line. This gas sparing circuit 2700 includes both the manual pilot control functionality of FIG. 3 (the manual pneumatic pilot control line 365 and the pilot air flow control switch 125) and the pneumatic timer pilot control of FIG. 10 for auto breath capability.

Operation of the gas sparing circuit 2700, with manual pilot control and pneumatic timer activated pilot control for auto breath capability, is now described. Operation of the gas sparing circuit 2700 is identical in operation to the gas sparing circuit 300 in FIG. 3 when the pneumatic valve/switch actuator 2702 is in the manual control position for utilization of the pilot circuit portion 320C in conjunction with pilot control line 365 and flow control switch 125. In this configuration, when the pneumatic valve/switch actuator 2702 is set in the manual position the pneumatic timers 1010 and 1020 are not active and pilot flow bypasses the timers and is directed to pilot control line 320C. When the pilot control line 365 is occluded by use of flow control switch 125, pilot circuit 320C is also occluded allowing pilot gas to flow through line 2701B and into pilot line 320D. Pilot gas at pressure $P_B$ is applied to the control side 333 of the gas sparing valve 330 and the valve opens allowing gas to flow into the main gas side 310 as described above with respect to FIGS. 3, 6, and 7. Releasing mask switch 125 causes the pressure to drop in pilot line 320D and at control side 333 of the gas sparing valve and the valve closes stopping gas flow into the main gas side 310 as described above with respect to FIGS. 3, 6, and 7. When the pneumatic valve/switch actuator 2702 is set in the auto breath position, the pneumatic timer circuit is activated and auto breath operation occurs in an automatic manner. When the pneumatic valve/switch actuator 2702 is set in the auto breath position pilot gas is directed to the pneumatic timer through line 1030A and operation occurs in the same manner as described with respect to gas sparing circuit 1000 in FIG. 10. At this time the pneumatic timers 1010 and 1020 begin to cycle the pilot gas flow on and off based on used selected time settings, to the gas sparing valve 330. In the first part of the timer cycle pilot gas is directed from the timer circuit through line 1030E to pilot line 320D and at control side 333 of the gas sparing valve 330 and the valve opens to allow gas flow through main gas side 310. In the second part of the timer cycle pilot gas flow is stopped to the gas sparing valve 300 at control side 333 which allows the pilot control line 320D to vent and the pressure at control side 333 to drop to Patm, closing the gas sparing valve 330 and stopping flow in the main gas side 310. The pneumatic timers 1010 and 1020 cycles the gas sparing valve 330 between the closed and open state creating a controlled auto breath function that can be user adjusted for on time and off time. This operation continues until the pneumatic valve/switch actuator 2702 is set back to the manual position or gas pressure is removed from the pilot line.

It is to be understood that the gas sparing circuit 2700 may be modified as described herein to provide for CPAP functionality as shown in FIG. 4 and/or to include an internal gas supply.

Figure 28:
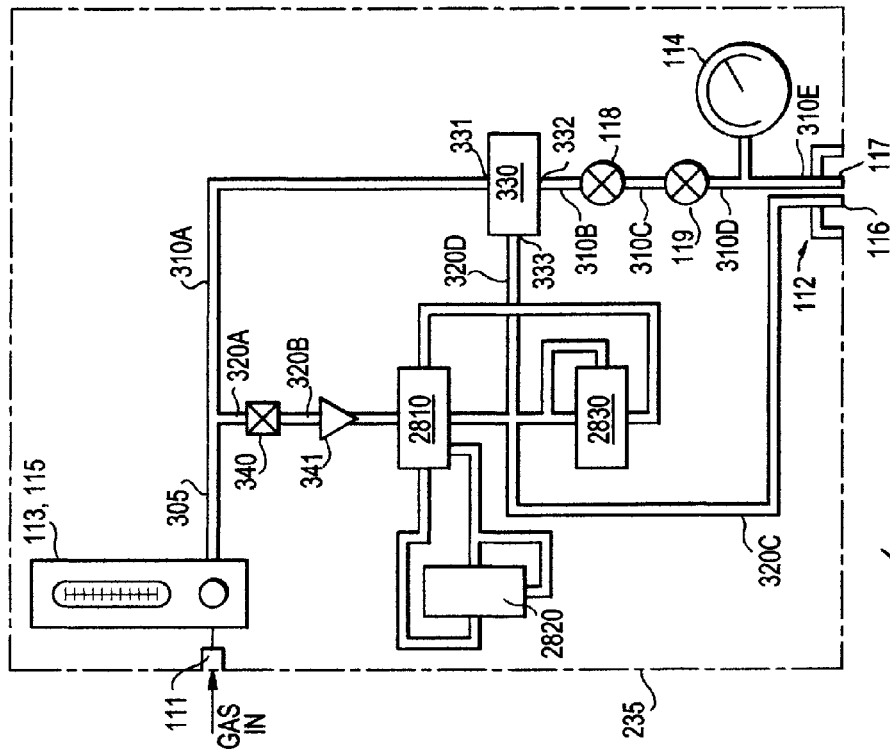
FIG. 28 illustrates an exemplary block diagram of an exemplary embodiment of a gas sparing circuit using a timer control for main-flow on-time and off-time control implemented with two on-time timers, in accordance with an exemplary embodiment of the present invention.

FIG. 28 illustrates a block diagram for a further exemplary embodiment of a gas sparing circuit 2800, in accordance with an exemplary embodiment of the present invention. This gas sparing circuit is similar to the gas sparing circuit 1000 illustrated in FIG. 10. As described herein, the gas sparing circuit 1000 uses an on-timer 1020 and an off-timer 1030 to control the auto breath circuit 1000. The gas sparing circuit in FIG. 28 uses two on-timers 2820, 2830, and a 4-way spool valve 2810 to effectively make one on-timer (the on-timer 2830) and an off-timer (the other on-timer 2820), without having to use a real off-timer, to control the pneumatically timing circuit 2800. The result is a gas sparing circuit that has the same control of inhalation and exhalation breath as the circuit 1000. In this gas sparing circuit 2800, as in the gas sparing circuit 1000, auto breath operation is activated through occlusion of the pilot line 365 at switch 125. Auto breath function stops when the pilot line 365 is un-occluded at mask switch 125.

It is to be understood that the gas sparing circuit 2800 may be modified as described herein to provide for CPAP functionality as shown in FIG. 4 and/or to include an internal gas supply.

Figures 29, 32:
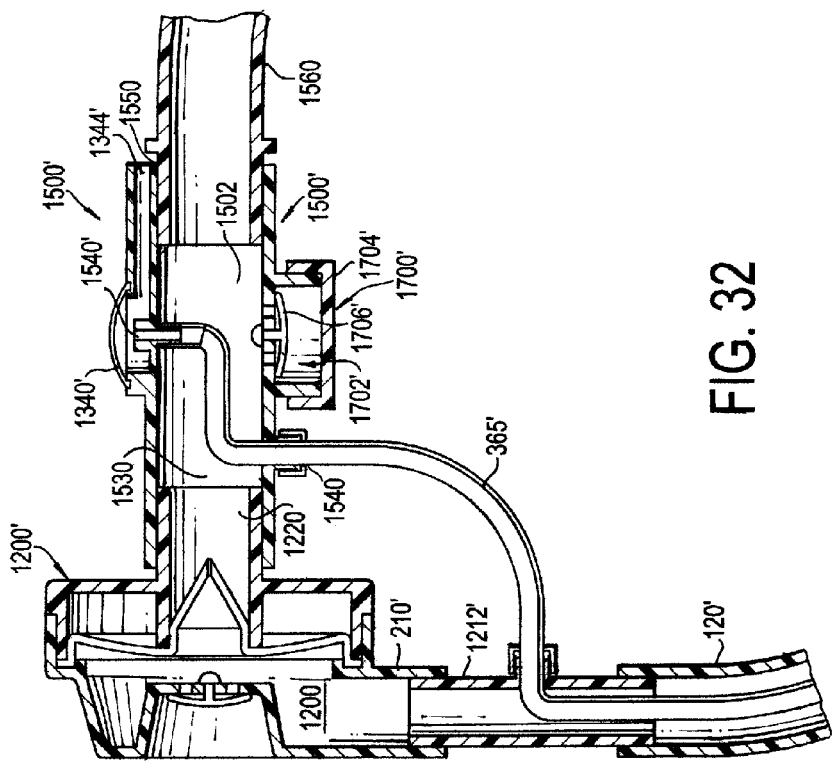
FIG. 29 illustrates an exemplary block diagram of an exemplary embodiment of a gas sparing circuit using selectable manual pilot line control of a gas sparing valve and pneumatic timer for main-flow on-time and off-time control utilizing two on-time timers, in accordance with an exemplary embodiment of the present invention.
FIG. 32 illustrates an exemplary embodiment of an endotracheal hand piece for control operation of a gas sparing circuit including a CPAP port for CPAP functionality, in accordance with an exemplary embodiment of the present invention.

FIG. 29 illustrates and describes a block diagram for another exemplary embodiment of a gas sparing circuit 2900, in accordance with an exemplary embodiment of the present invention. This gas sparing circuit is similar to the gas sparing circuit 2700 in FIG. 27 but uses two on-timers 2820 and 2830 and a 4-way spool valve 2810 to effectively make one on-timer (the on-timer 2830) and one off-time (the off-timer 2620), without having to have a real off-timer, to control the pneumatically timing circuit 2900. As with gas sparing circuit 2700 in FIG. 27, the function of the gas sparing circuit is activated by pneumatic valve/switch 2702 so that manual pilot control is still possible with this gas sparing circuit but the circuit can be switched into automatic auto breath mode without having to hold the external pilot line 365 occluded.

It is to be understood that the gas sparing circuit 2700 may be modified as described herein to provide for CPAP functionality as shown in FIG. 4 and/or to include an internal gas supply.

An exemplary feature which may be added to any of the exemplary embodiments of the gas sparing circuits described herein. In any of the gas sparing circuits having manual pilot control lines 365, a latch can be added to the switch 125 or 1340 or 2425 to allow the switch to be held closed without the need for the user to apply constant pressure to the switch 125 or 1340 or 2425. This latch may be desirably used for auto breath modes to allow the user to not have to hold the switch 125 or 1340 or 2425 down continuously.

Figure 30:
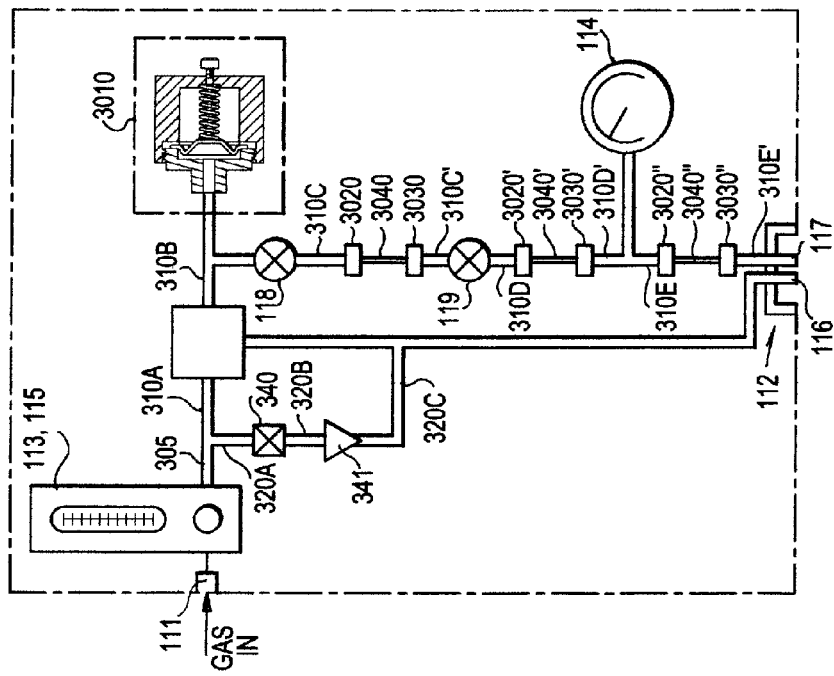
FIG. 30 illustrates an exemplary block diagram of an exemplary embodiment of a gas sparing circuit comprising a pressure surge damping element to eliminate pressure surges when a gas sparing valve is opened, in accordance with an exemplary embodiment of the present invention.

Now referring to FIG. 30, there is illustrated an exemplary embodiment of a gas sparing circuit 3000 which functions similarly to the gas sparing circuit 300 of FIG. 3, but further includes a pressure surge damper configuration, in accordance with an exemplary embodiment of the present invention. The pressure surge damper configuration comprises a series of damping elements comprising reducing elements 3020, reduced tube ID sections 3040, and expansion elements 3030 in exemplary positions to dampen gas pressure surges that may occur in the main gas line 310B when the gas sparing valve 330 opens. It is to be understood that this pressure surge damper configuration may be added to any of the exemplary gas sparing circuits described herein.

Operation of the pressure surge damper configuration using reducing elements 3020, reduced ID elements 3040, and expansion elements 3030 is now described. Referring to FIG. 30, as the gas sparing valve 330 opens pressurized gas quickly flows into the main gas line 310B. This instant release of pressurized gas flow can create a pressure wave front in the main gas line 310C, 310D and 310E that may be slightly higher than the steady state pressure after the gas sparing valve 330 has been opened for a period of time. It may therefore be beneficial to dampen this pressure surge using a pressure surge damper system containing damping elements 3020, 3030 and 3040 as illustrated. As the gas pressure front moves along main gas line 310B it encounters the reducer element 3020 in the main gas line. The gas pressure enters the reducer 3020 where the flow path ID is decreased abruptly creating a velocity increase in the gas flow and a turbulence effect. The gas flow then traverses through a reduced ID flow element 3040 and then enters an expansion element 3030 where the flow path ID is increased abruptly creating a velocity decrease and a second turbulent effect which combines to reduce the pressure wave an incremental amount. Additional elements located at 3020', 3030' and 3040' and at 3020", 3030" and 3040" are added to further dampen the pressure surge to the desired level. By combining a series of these elements in series, or if desired in parallel, the pressure wave front can be either partially suppressed or fully suppressed as desired. As the initial pressure surge damper elements 3020, 3030, and 3040 act to dampen the pressure wave front, the main gas with a reduced pressure wave progresses through main gas line 310C' to line 310D and then to damping elements 3020', 3030' and 3040' where the pressure wave front is reduced further. The main gas then progresses through main line 310D' with even further reduction in the amplitude of the pressure wave front to main line 310E. The gas then interacts with the damping element 3020", 3030" and 3040" where again the pressure wave front is further reduced to the point where it is totally eliminated and the main gas, without the pressure wave front, then progresses to the reaming main gas lines 310E' and into the breathing circuit 120 at outlet 117. When the gas sparing valve 330 is closed, and the gas flow in the main gas line 310B ceases. The pressure surge damper configuration is then ready for the next pressure wave.

Figure 30A:
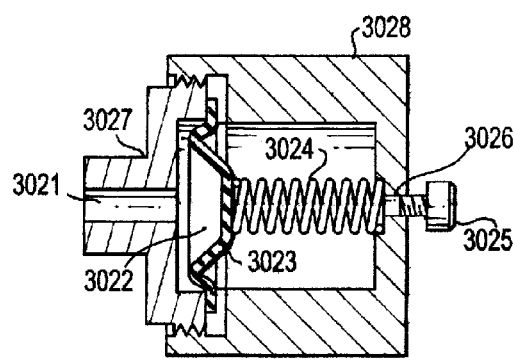
FIG. 30A illustrates an exemplary embodiment of the pressure surge dampening element of FIG. 30, in accordance with an exemplary embodiment of the present invention.

In an exemplary alternative embodiment, a pressure surge damper 3010 may be used in place of or in addition to the dampening elements illustrated in FIG. 30 and described above. FIG. 30A illustrates an exemplary embodiment of the damper 3010, in accordance with an exemplary embodiment of the present invention. The pressure surge damper contains a base 3027, with inlet port 3021, a pliant damper diaphragm 3023, a spring 3024, a vent control valve 3025 with vent port 3026, and a cap 3028. The diaphragm 3023, cap 3028, and base 3027 interact to create a sealed damper chamber 3022. This pressure damper is shown in the unpressurized state.

Operation of the pressure surge damper 3010 is now described. Referring to FIGS. 30 and 30A, as the gas sparing valve 330 opens pressurized gas quickly flows into main gas line 310B. This instant release of pressurized gas flow can create a pressure wave front in the main gas line 310C, 310D and 310E that may be slightly higher than the steady state pressure after the gas sparing valve has been opened for a period of time. It may therefore be beneficial to dampen this pressure surge using a pressure surge damper 3010 as illustrated. As the gas pressure front moves along main gas line 310B it encounters the pressure surge damper 3010 at a 90 degree bend in the main gas line. The gas pressure enters the inlet port 3021 of the pressure surge damper and encounters the pliant damper diaphragm 3023. The gas pressure fills the sealed damper chamber 3022 and forces the damper diaphragm to expand and move against the spring 3024. The air trapped behind the pliant diaphragm is compressed and in a controlled manner exits through the vent port 3026. The vent control valve 3025 controls the rate at which the air can be vented from the space behind the pliant diaphragm and thus the rate at which the pliant diaphragm can expand and move against the spring. The pliant diaphragm 3023 in combination with the spring 3024 and the vent control valve 3025 act together to create a controlled damping effect on the main gas entering the inlet port. As the pressure surge damper 3010 acts to dampen the pressure wave, the pliant diaphragm 3023 reaches its full equilibrium travel and the main gas without the pressure wave then progresses to the reaming main gas lines 310C, 310D, 310E and into the breathing circuit 120.

When the gas sparing valve 330 is closed, and the gas flow in the main gas line 310B ceases, the pliant diaphragm 3023 returns to its original unpressurized condition by reaction force of the spring 3024. The pressure surge damper is then ready for the next pressure wave.

Figure 31A:
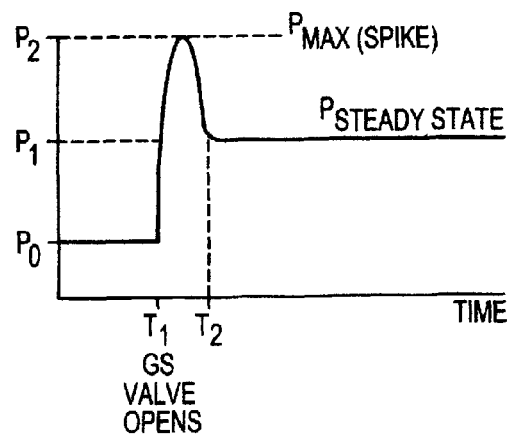
FIG. 31A illustrates a graph of exemplary gas pressure through the primary branch in the exemplary embodiment of the gas sparing circuit illustrated in FIG. 3, in accordance with an exemplary embodiment of the present invention.
Figure 31B:
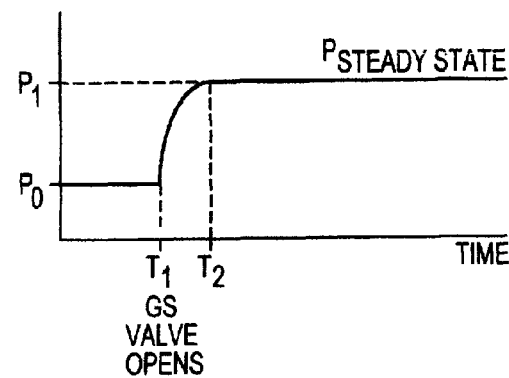
FIG. 31B illustrates a graph of exemplary gas pressure through the primary branch in the exemplary embodiment of the gas sparing illustrated in FIG. 30, in accordance with an exemplary embodiment of the present invention.

FIGS. 31A and 31B illustrate the damping effect of the pressure surge damper 3010 in the gas sparing circuit 3000. FIG. 31A illustrates the pressure in the main gas line after the time $T_1$ that the gas sparing valve 330 opens without the pressure surge damper. The pressure in the main gas line 310 increase quickly to $P_2$ which is the surge pressure and is above the steady state pressure $P_1$. The pressure then drops at time $T_2$ to the steady state pressure $P_1$. FIG. 31B illustrates the pressure in the main gas line after the time $T_1$ that the gas sparing valve 330 opens with the pressure surge damper. The pressure in the main gas line 310 is damped and slowly increases to $P_1$, the steady state pressure at time $T_2$. The pressure wave in the main gas line 310 is suppressed and no pressure spike occurs at the breathing circuit 120.

FIG. 32 illustrates an exemplary alternative embodiment of the endotracheal (ET) hand piece 1500 of FIG. 15, generally designated as 1500' in FIG. 32, in accordance with an exemplary embodiment of the present invention. The ET hand piece 1500' includes several similarities with the ET hand piece 1500. For example, the inlet port 1530 of the ET hand piece 1500' is configured to be connected to the rotating outlet port 1220 of the mask connection 1200, and the outlet port 1550 of the ET hand piece 1500' is configured to be connected to the endotracheal tube 1560. Furthermore, the ET hand piece 1500' includes the pilot control switch 1340', as does the ET hand piece 1500, but further includes a CPAP vent port 1700' containing the CPAP valve 1706' and port cap 1704' as described in FIGS. 22 and 23, which the ET hand piece 1500 does not contain. When used in conjunction with the gas sparing circuit 400 of FIG. 4 set to CPAP mode, the port cap 1704' is removed from the valve housing 1702' and CPAP functionality is possible.

It is to be understood that the ET hand piece 1500' may be modified as described herein to include electrical wires such as those illustrated in FIG. 24, element 2465, and an electrical switch similar to switch 2425 in FIG. 24 to allow functionality with the gas sparing circuit 2400 shown in FIG. 24.

Because the various embodiments of the gas sparing systems, devices, and circuits described herein provide for control of main (primary) gas, large continuous gas flows are minimized, and gas is conserved. In addition, the gas sparing systems, devices, and circuits described herein allow for precise pressure and volume control. Several examples of patient interfaces, such as the masks 130, 130', 130", and 130'" and ET hand pieces 1500 and 1500', are described herein for delivering the gas to a patient. It is to be understood that the patient interfaces are not limited to these examples.

These and other advantages of the present invention will be apparent to those skilled in the art from the foregoing specification. For example, it is contemplated that the gas sparing valve 330 and the pilot control line 365 may be replaced, respectively, by an electronically controlled valve and a switch coupled to the valve via a conductor for selective control of the valve. Further, the pneumatic timer controls may be replaced by electrical timer controls. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. A system for delivering gas to a patient, comprising:
a gas control unit comprising an outlet comprising a main gas line outlet and a pilot control line outlet, the gas control unit further comprising a gas sparing circuit comprising a primary branch coupled to the main gas line outlet and a pilot control branch coupled to the pilot control line outlet, the primary branch comprising a gas sparing valve coupled to the pilot control branch for controlling a flow of gas through the primary branch;
a breathing circuit comprising a main gas line comprising a first end and a second end, the first end of the main gas line coupled to the main gas line outlet, the breathing circuit further comprising a pilot control line comprising a first end and a second end, the first end of the pilot control line coupled to the pilot control line outlet;
a pilot control switch coupled to the second end of the pilot control line, the pilot control switch configured for:
selectively venting gas in the pilot control line to atmosphere to cause the gas sparing valve to prevent the flow of gas to the main gas line via the main gas line outlet; or
selectively occluding the pilot control line to cause the gas sparing valve to provide the flow of gas to the main gas line via the main gas line outlet; and
a patient interface coupled to the second end of the main gas line of the breathing circuit.

2. The system of claim 1, wherein:
the pilot control switch is a pneumatic control switch for selectively venting gas in the pilot control line to atmosphere or occluding the pilot control line, and
the gas sparing valve is a pneumatic control valve disposed in the primary branch, the pilot control switch configured to actuate the pneumatic control valve based on the selective occlusion of the pilot control line by the pneumatic control switch to provide the flow of gas to the main gas line via the main gas line outlet.

3. The system of claim 2, wherein the patient interface is a mask coupled to the second end of the main gas line of the breathing circuit, and the pneumatic control switch is disposed on the mask.

4. The system of claim 2, wherein the patient interface is an endotracheal tube adapter for connection to an endotracheal tube, and the pneumatic control switch is disposed on the endotracheal tube adapter.

5. The system of claim 1, wherein:
the gas control unit further comprises a continuous positive airway pressure (CPAP) branch coupled to the main gas outlet, and a mode-selection switch for selectively directing source gas to the CPAP branch or to the gas sparing circuit, and
the patient interface is a mask coupled to the second end of the main gas line of the breathing circuit, the mask comprising a CPAP exhalation port.

6. The system of claim 1, wherein the gas control unit further comprises an internal air supply that sources the flow of gas to the main gas line, and wherein the primary branch is further coupled to internal air supply.

7. The system of claim 1, wherein the pilot control switch is a pneumatic-mechanical timer-based trigger.

8. A gas control unit for delivering gas to a patient, comprising:
an outlet comprising a main gas line outlet and a pilot control line outlet; and
a gas sparing circuit comprising:
a primary branch coupled to the main gas line outlet;
a pilot control branch coupled to the pilot control line outlet; and
a gas sparing valve coupled to the pilot control branch for:
allowing a flow of gas to the main gas outlet in response to selective venting of gas in the pilot control branch to atmosphere; or
preventing the flow of gas to the main gas outlet in response to selective occlusion of the pilot control branch.

9. The gas control unit of claim 8, wherein:
the gas sparing valve is a pneumatic control valve comprising a pneumatic control input coupled to the pilot control branch, the pneumatic control valve disposed in the primary branch and configured to actuate in response to the selective occlusion of the pilot branch by the pneumatic control switch to provide the flow of gas to the main gas line outlet.

10. The gas control unit of claim 9, further comprising a first pneumatic timer control disposed in the pilot control branch, the first pneumatic timer control configured to control an on-time of the pneumatic control valve in response to the selective control to provide the flow of gas to the main gas line outlet.

11. The gas control unit of claim 10, further comprising a second pneumatic timer control disposed in the pilot control branch, the second pneumatic timer control configured to control an off-time of the pneumatic control valve in response to the selective control to provide the flow of gas to the main gas line outlet.

12. The gas control unit of claim 8, further comprising a continuous positive airway pressure (CPAP) branch coupled to the main gas outlet, and a mode-selection switch for selectively directing source gas to the CPAP branch or to the gas sparing circuit.

13. A patient interface for use with a gas sparing circuit for delivering gas to a patient, comprising:
a main gas line comprising an output for delivering the gas to the patient and an input for receiving the gas from a source;
a pilot control line; and
a pilot control switch coupled to the pilot control line, the pilot control switch configured for:
selectively venting gas in the pilot control line to atmosphere to prevent the delivery of the gas to the patient; or
selectively occluding the pilot control line to cause the delivery of the gas to the patient.

14. The patient interface of claim 13, wherein the control switch is a pneumatic switch.

15. The patient interface of claim 13, further comprising a vent port for exhalation by a user of the patient interface during a continuous positive airway pressure (CPAP) mode.

16. The patient interface of claim 13, further comprising a valve system providing for one-way flow of the gas to the output during an inhalation phase of a resuscitation mode and for a spontaneous breath, and one-way flow of exhalation though the valve system during an exhalation phase of the resuscitation mode.

17. The patient interface of claim 13, wherein the output is a patient-mask interface.

18. The patient interface of claim 13, wherein the output is an endotracheal tube connection.

* * * * *